US012799487B2

(12) United States Patent
McEachin

(10) Patent No.: US 12,799,487 B2
(45) **Date of Patent: *Nov. 17, 2026**

(54) ANTISENSE OLIGONUCLEOTIDES THAT BIND NUCLEIC ACIDS ENCODING ELAVL3 CRYPTIC EXONS

(71) Applicant: Emory University, Atlanta, GA (US)

(72) Inventor: Zachary McEachin, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/637,013

(22) Filed: Apr. 2, 2026

(65) Prior Publication Data

US 2026/0209765 A1 Jul. 23, 2026

Related U.S. Application Data

(63) Continuation-in-part of application No. PCT/US2024/049647, filed on Oct. 2, 2024.

(60) Provisional application No. 63/930,211, filed on Dec. 3, 2025, provisional application No. 63/917,589, filed on Nov. 14, 2025, provisional application No. 63/541,983, filed on Oct. 2, 2023.

(51) Int. Cl.

| | |
|---|---|
| ***C12N 15/113*** | (2010.01) |
| ***A61K 31/7115*** | (2006.01) |
| ***A61K 31/712*** | (2006.01) |
| ***A61P 25/28*** | (2006.01) |

(52) U.S. Cl.

CPC ........ *C12N 15/113* (2013.01); *A61K 31/7115* (2013.01); *A61K 31/712* (2013.01); *A61P 25/28* (2018.01); *C12N 2310/11* (2013.01); *C12N 2310/321* (2013.01); *C12N 2310/3231* (2013.01); *C12N 2310/334* (2013.01)

(58) Field of Classification Search

CPC .............. C12N 15/113; C12N 2310/11; C12N 2310/321; C12N 2310/3231; A61K 31/7115; A61K 31/712; A61P 25/28

See application file for complete search history.

(56) References Cited

U.S. PATENT DOCUMENTS

| | | | |
|---|---|---|---|
| 2019/0112603 | A1 | 4/2019 | Jo et al. |
| 2022/0133848 | A1 | 5/2022 | Eggan et al. |

FOREIGN PATENT DOCUMENTS

| | | | |
|---|---|---|---|
| WO | WO2012156515 A1 | 11/2012 | |
| WO | WO2021195446 A2 | 9/2021 | |

OTHER PUBLICATIONS

International Search Report for PCT/US2024/049647 mailed Dec. 11, 2024.

Costantino et al., Alternatively spliced ELA VL3 cryptic exon 4a causes ELA VL3 downregulation in ALS TDP-43 proteinopathy. Acta Neuropathol. 2024, vol. 147(1):93. PDF File: p. 1-4 Entire documentation especially Abstract; and p. 2, Fig 1.

(Continued)

*Primary Examiner* — Terra C Gibbs

(74) *Attorney, Agent, or Firm* — Thomas | Horstemeyer, LLP

(57) ABSTRACT

Antisense oligonucleotides that specifically bind an ELAV-like RNA-binding protein 3 (ELAVL3) cryptic exon DNA, pre-mRNA, mRNA, or nascent RNA sequence are provided. Methods of making and using the same are also provided.

20 Claims, 27 Drawing Sheets

Specification includes a Sequence Listing.

(56) References Cited

OTHER PUBLICATIONS

Susnjar et al., Cell environment shapes TDP-43 function with implications in neuronal and muscle disease. Commun Biol. 2022, vol. 5:314. PDF File: p. 1-17 Entire documentation especially Abstract; p. 6, col. 2, last para; p. 7, col. 1, top para; and p. 8, Fig 6.

Ogawa et al., Elavl3 is essential for the maintenance of Purkinje neuron axons. Sci Rep. 2018. vol. 8(1):2722. PDF File: p. 1-13 Entire documentation especially Abstract; p. 3, Fig 1; and p. 8, Fig 5.

Diaz-Garcia et al., Nuclear depletion of RNA-binding protein ELA VL3 (HuC) in sporadic and familial amyotrophic lateral sclerosis. Acta Neuropathol. 2021, vol. 142(6), p. 985-1001. Entire documentation especially Abstract; p. 986, col. 1, and col. 2, para 1; and p. 995, Fig 5.

Raguraman et al., Drug delivery approaches for HuR-targeted therapy for lung cancer. Adv Dmg Deliv Rev. 2022, vol. 180:114068. PDF File: p. 1-23 Entire documentation especially Abstract; p. 2, col. 2, lower para; p. 3, col. 1, up para, and col. 2, lower para; p. 5, Fig 1; p. 6, Table 3; and p. 14, Fig 5.

PubChem_ CID _132019842, (7S)-I-(hydroxymethyl)-2,5-dioxabicyclo[2.2. I ]hep tan-7-ol. PubChem CID 132019842. PubChem release 2021. [online]. [Retrieved on Oct. 31, 2024]. [Retrieved from the Internet: URL: https://pubchem.ncbi.nlm.nih.gov/compound/132019842] Title; PubChem CID; and Structure.

Calliari et al. "HDGFL2 cryptic proteins report presence of TDP-43 pathology in neurodegenerative diseases." Molecular Neurodegeneration. 2024, vol. 19:29.

Ince-Dunn et al. "Neuronal Elav-like (Hu) proteins regulate RNA splicing and abundance to control glutamate levels and neuronal excitability." Neuron. 2012, vol. 75(6): 1067-1080.

Irmady et al. "ELAVL3 regulates splicing of RNAs encoding synaptic signaling proteins in D1 and D2 striatal medium spiny neurons." bioRxiv. 2024.

Irwin et al. "A fluid biomarker reveals loss of TDP-43 splicing repression in presymptomatic ALS-FTD." Nature Medicine. 2024, vol. 30: 382-393.

Krach et al. "Transcriptome-pathology correlation identifies interplay between TDP-43 and the expression of its kinase CK1E in sporadic ALS." Acta Neuropathol. 2018, vol. 136: 405-423.

Ling et al. "TDP-43 repression of nonconserved cryptic exons is compromised in ALS-FTD." Science. 2015, vol. 349 (6248): 650-655.

Seddighi et al. "Mis-spliced transcripts generate de novo proteins in TDP-43-related ALS/FTD." Sci Transl Med. 2024, vol. 16(734).

McEachin et al. "Chimeric peptide species contribute to divergent dipeptide repeat pathology in c9ALS/FTD and SCA36." Neuron. 2020, vol. 107(2): 292-305.

Mehta et al. "The era of cryptic exons: implications for ALS-FTD." Molecular Neurodegeneration. 2023, vol. 18: 16.

Newton et al. "TDP43 proteinopathy exhibits disease, tissue, and context-specific cryptic splicing signatures." bioRxiv. 2024.

Quattrone et al. "Posttranscriptional regulation of gene expression in learning by the neuronal ELAV-like mRNA-stabilizing proteins." PNAS. 2001, vol. 98(20): 11668-11673.

Newton et al. "Divergent TDP43-regulated and TDP43-independent cryptic splicing in the cortex and spinal cord." bioRxiv. 2025.

Ma et al. "TDP-43 represses cryptic exon inclusion in the FTD-ALS gene UNC13A." Nature. 2022, vol. 603: 124-130.

Trautwig et al. "Molecular Subtyping Based on Hippocampal Cryptic Exon Burden Reveals Proteome-wide Changes Associated with TDP-43 Pathology across the Spectrum of LATE and Alzheimer's Disease." bioRxiv. 2025.

ANTISENSE OLIGONUCLEOTIDES THAT BIND NUCLEIC ACIDS ENCODING ELAVL3 CRYPTIC EXONS

CROSS-REFERENCE TO RELATED APPLICATIONS

This application claims the benefit of U.S. Provisional Application No. 63/917,589, filed on Nov. 14, 2025, and U.S. Provisional Application No. 63/930,211, filed on Dec. 3, 2025. This application is also a continuation-in-part of International Application No. PCT/US2024/049647, filed on Oct. 2, 2024, which claims the benefit of U.S. Provisional Application No. 63/541,983, filed on Oct. 2, 2023. Each of these applications is incorporated by reference herein in its entirety.

SEQUENCE LISTING

A Sequence Listing has been submitted electronically in XML format and is hereby incorporated by reference in its entirety. The XML copy, created on Jun. 25, 2026, is named 80503_1071_Sequence_Listing_Updated.xml and is 21,583 bytes in size.

BACKGROUND

TDP-43 (TAR DNA-binding protein 43) is a highly conserved RNA-binding protein that plays critical roles in RNA metabolism, including transcription regulation, splicing, mRNA transport, and stability. Under normal conditions, TDP-43 resides primarily in the nucleus where it binds to thousands of RNA targets and regulates their processing. However, in disease states, TDP-43 becomes abnormally phosphorylated, ubiquitinated, and cleaved, forming cytoplasmic aggregates while being depleted from the nucleus. This pathological hallmark—nuclear clearance and cytoplasmic aggregation—is found in approximately 97% of ALS cases and 45% of frontotemporal dementia (FTD) cases, making TDP-43 proteinopathy one of the most common features of neurodegenerative disease.

ALS is a fatal motor neuron disease characterized by progressive paralysis and typical survival of two to five years post-diagnosis. The discovery of TDP-43 pathology in ALS in 2006 revolutionized understanding of the disease. In nearly all non-SOD1 ALS cases, motor neurons exhibit the characteristic TDP-43 cytoplasmic inclusions and nuclear depletion. Mutations in the TARDBP gene (encoding TDP-43) cause familial ALS, though these mutations account for only 1-2% of ALS cases. More importantly, the loss of nuclear TDP-43 function appears to be a central driver of neurodegeneration across both familial and sporadic ALS. This nuclear depletion leads to widespread RNA processing defects, including aberrant splicing, which directly contributes to motor neuron death. Recent therapeutic strategies, including the use of antisense oligonucleotides, are being developed to target downstream consequences of TDP-43 dysfunction (see, e.g., PCT/US2021/024254, which is incorporated by reference herein in its entirety).

While traditionally defined by amyloid plaques and tau tangles, Alzheimer's disease (AD) frequently exhibits TDP-43 pathology—a condition termed LATE (limbic-predominant age-related TDP-43 encephalopathy) when occurring in the absence of other pathologies. Studies indicate that 30-50% of AD patients show TDP-43 co-pathology, particularly in older individuals and those with more severe cognitive impairment. TDP-43 in AD tends to accumulate in the hippocampus and amygdala, correlating with accelerated cognitive decline and greater memory impairment and hippocampal atrophy compared to "pure" AD cases. The presence of TDP-43 pathology in AD suggests convergent mechanisms across neurodegenerative diseases and raises questions about whether targeting TDP-43 dysfunction could benefit multiple disease populations.

One of the most significant discoveries regarding TDP-43 function is its role in suppressing cryptic exons—normally silent sequences within introns that become aberrantly included in mature mRNA when TDP-43 is depleted from the nucleus. TDP-43 typically binds to long intronic UG-rich sequences near these cryptic splice sites, preventing their recognition by the splicing machinery. When nuclear TDP-43 levels drop due to pathological aggregation, cryptic exons are incorporated into transcripts, often introducing premature stop codons that trigger nonsense-mediated decay or produce truncated, nonfunctional proteins. Hundreds of transcripts undergo pathological mis-splicing (cryptic exon inclusion) upon nuclear depletion or dysfunction of TDP-43, including ELAV-like RNA-binding protein 3 (ELAVL3), Stathmin-2 (STMN2), PTPRN2, GRAM Domain Containing 1A (GRAMD1A), Glutathione Peroxidase 7 (GPX7), Calcium/calmodulin-dependent protein kinase II beta (CAMK2B), UNC13A, and HDGFL2.

A need exists for further strategies, including more broadly impactful antisense oligonucleotides, to target downstream consequences of TDP-43 dysfunction.

SUMMARY

In one aspect, an antisense oligonucleotide (ASO) is provided.

In one aspect, the ASO may comprise a DNA sequence comprising one or more of SEQ ID NOs: 6-9 or a DNA sequence comprising a segment of five contiguous nucleotides of any one of SEQ ID NOs: 6-9.

In one aspect, the ASO is characterized in that it: (i) specifically binds an ELAVL3 cryptic exon (CE) DNA or RNA sequence in a cell when introduced into the cell; and (ii) increases ELAVL3 protein expression in the cell relative to a cell in which the ASO has not been introduced. In one aspect, the ASO is further characterized in that it increases STMN2 protein expression in the cell relative to a cell in which the ASO has not been introduced.

In one aspect, the ASO further comprises a deoxyribose sugar modification.

In one aspect, the ASO is characterized in that two or more adjacent nucleosides are connected via a phosphate linkage. In one aspect, the phosphate linkage is a phosphorothioate, methylphosphonate, or phosphorodiamidate linkage.

In one aspect, a recombinant vector is provided, the recombinant vector encoding the ASO.

In one aspect, a pharmaceutical composition is provided, the pharmaceutical composition comprising the ASO.

In one aspect, a method is provided for treating or preventing a neurodegenerative disease, the method comprising administering an effective amount of an ASO comprising a DNA sequence comprising one or more of SEQ ID NOs: 6-9 or a DNA sequence comprising a segment of five contiguous nucleotides of any one of SEQ ID NOs: 6-9, or administering an effective amount of a recombinant vector encoding the ASO, or administering an effective amount of a pharmaceutical composition comprising either the ASO or a recombinant vector encoding the ASO to a subject in need thereof. In one aspect, the neurodegenerative disease is associated with a TDP-pathology or a decline in TDP-43 functionality in neuronal cells.

In another aspect, the ASO may comprise an RNA sequence comprising one or more of SEQ ID NOs: 15-18 or an RNA sequence comprising a segment of five contiguous nucleotides of any one of SEQ ID NOs: 15-18. In one aspect, the ASO is characterized in that it: (i) specifically binds an ELAVL3 cryptic exon (CE) DNA or RNA sequence in a cell when introduced into the cell; and (ii) increases ELAVL3 protein expression in the cell relative to a cell in which the ASO has not been introduced. In one aspect, the ASO is further characterized in that it increases STMN2 protein expression in the cell relative to a cell in which the ASO has not been introduced.

In one aspect, the ASO further comprises a ribose sugar modification. In one aspect, the sugar modification comprises a 2'-O-methoxyethyl (MOE) modification.

In one aspect, the ASO is characterized in that two or more adjacent nucleosides are connected via a phosphate linkage. In one aspect, the phosphate linkage is a phosphorothioate, methylphosphonate, or phosphorodiamidate linkage.

In one aspect, a recombinant vector is provided, the recombinant vector encoding the ASO.

In one aspect, a pharmaceutical composition is provided, the pharmaceutical composition comprising the ASO.

In one aspect, a method is provided for treating or preventing a neurodegenerative disease, the method comprising administering an effective amount of an ASO comprising an RNA sequence comprising one or more of SEQ ID NOs: 15-18 or an RNA sequence comprising a segment of five contiguous nucleotides of any one of SEQ ID NOs: 15-18, or administering an effective amount of a recombinant vector encoding the ASO, or administering an effective amount of a pharmaceutical composition comprising either the ASO or a recombinant vector encoding the ASO to a subject in need thereof. In one aspect, the neurodegenerative disease is associated with a TDP-pathology or a decline in TDP-43 functionality in neuronal cells.

DETAILED DESCRIPTION

Definitions

Figure 1:
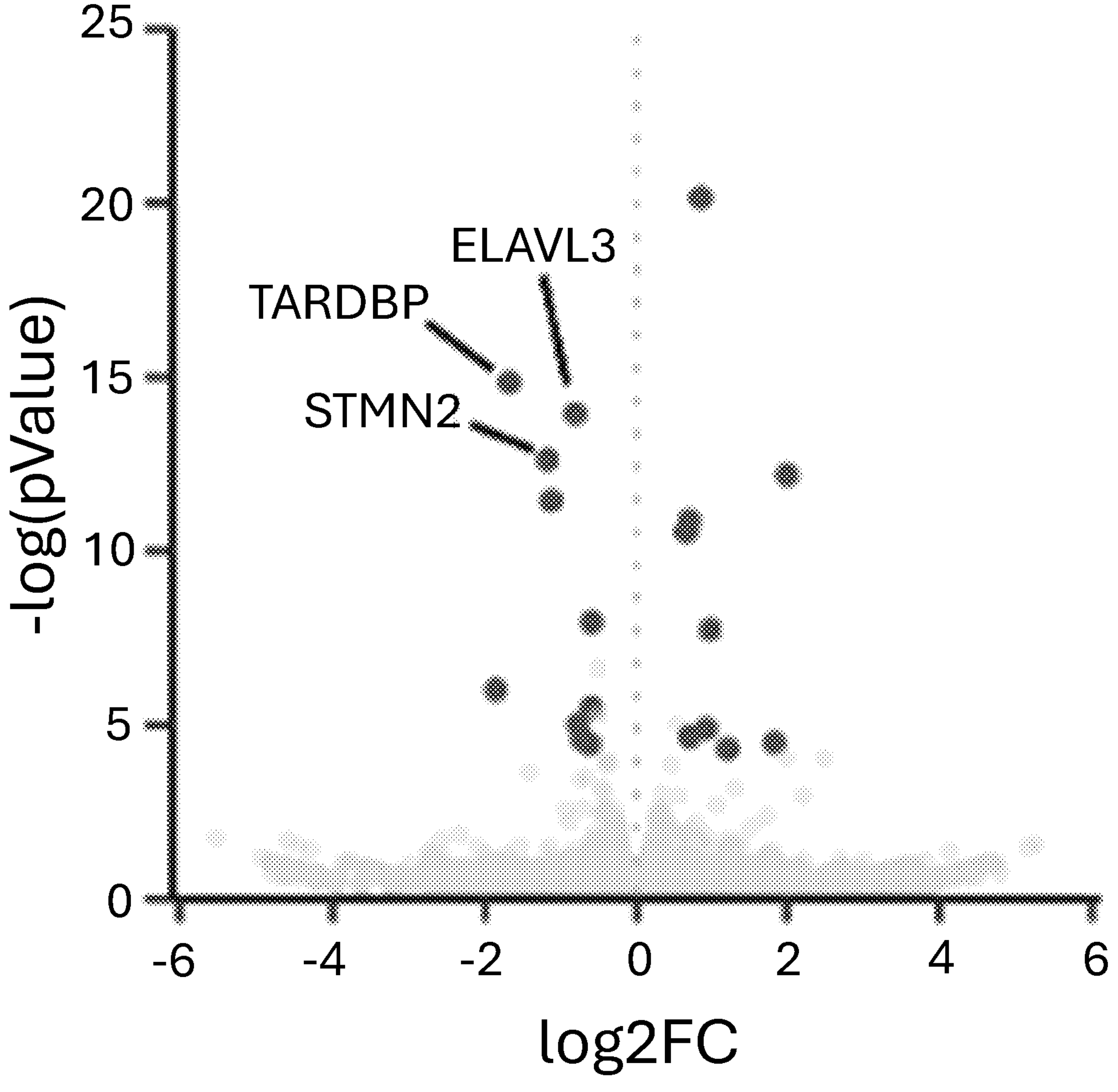
FIG. 1 shows the proteomic fingerprint of iPSC-derived human neurons under conditions of reduced TDP-43 expression compared to cells treated with a control siRNA.

Unless otherwise specified or indicated by context, the terms "a," "an," and "the" mean "one or more." For example, "an ASO" should be interpreted to mean "one or more ASOs." As used herein, "about," "approximately,"

“substantially,” and “significantly” will be understood by persons of ordinary skill in the art and will vary to some extent based on the context in which they are used. If there are uses of these terms that are not clear to persons of ordinary skill in the art given the context in which they are used, “about” and “approximately” will mean plus or minus ≤10% of the particular term, and “substantially” and “significantly” will mean plus or minus >10% of the particular term. As used herein, the terms “include” and “including” have the same meaning as the terms “comprise” and “comprising” in that these latter terms are “open” transitional terms that do not limit claims only to the recited elements succeeding these transitional terms. The term “consisting of,” while encompassed by the term “comprising,” should be interpreted as a “closed” transitional term that limits claims only to the recited elements succeeding this transitional term. The term “consisting essentially of,” while encompassed by the term “comprising,” should be interpreted as a “partially closed” transitional term that permits additional elements, but only if those additional elements do not materially affect the basic and novel characteristics of the invention claimed. As used herein, the term “subject” may be interchangeable with “patient” or “individual” and means an animal, which may be a human or non-human animal, in need of treatment. A “subject in need of treatment” may include a subject having a disease, disorder, or condition that is responsive to therapy with a compound or pharmaceutical composition as described herein, which is targeted to ASOs that specifically bind ELAVL3 RNA or DNA sequence(s) coding for a CE. For example, a “subject in need of treatment” may include a subject having a neurodegenerative disease. “Neurodegenerative disorder” or “neurodegenerative disease” refers to a disease condition involving neural loss mediated or characterized at least partially by deterioration of a neural cell, neural stem cell, or neural progenitor cell. Non-limiting examples of neurodegenerative disorders include polyglutamine expansion disorders (e.g., HD, Kennedy’s disease (also referred to as spinobulbar muscular atrophy), and spinocerebellar ataxia (e.g., type 1, type 2, type 3 (also referred to as Machado-Joseph disease), type 6, type 7, and type 17)), other trinucleotide repeat expansion disorders (e.g., fragile X syndrome, fragile XE mental retardation, Friedreich’s ataxia, myotonic dystrophy, spinocerebellar ataxia type 8, and spinocerebellar ataxia type 12), Alexander disease, Alper’s disease, AD, LATE, ALS, ataxia telangiectasia, Batten disease, Canavan disease, Cockayne syndrome, corticobasal degeneration, Creutzfeldt-Jakob disease, Guillain-Barre syndrome, ischemia stroke, Krabbe disease, kuru, Lewy body dementia, multiple sclerosis, multiple system atrophy, Chorea, Parkinson’s disease, Pelizaeus-Merzbacher disease, Pick’s disease, primary lateral sclerosis, progressive supranuclear palsy, spinal cord injury, spinal muscular atrophy (SMA), and FTD, and other neurological disorders that cause memory or cognitive disfunction such as memory loss, speech impediments, autism, etc. In some contexts, neurodegenerative disorders encompass neurological injuries or damages to the CNS or PNS associated with physical injury (e.g., head trauma, concussions, mild to severe traumatic brain injury (TBI), diffuse axonal injury, cerebral contusion, acute brain swelling, and the like).

As used herein, the term “pharmaceutically acceptable” refers to those agents, materials, compositions, or dosage forms that are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase “effective amount” shall mean that drug dosage that provides the specific pharmacological response for which the drug is administered in a significant number of subjects in need of such treatment. An effective amount of a drug that is administered to a particular subject in a particular instance will not always be effective in treating the conditions/diseases described herein, even though such dosage is deemed to be a therapeutically effective amount by those of skill in the art.

The terms “nucleobase polymer” and “ASO” or “antisense oligonucleotide” are used interchangeably herein and refer to a polymer comprising nitrogen containing aromatic or heterocyclic bases that bind to naturally occurring nucleic acids through hydrogen bonding otherwise known as base pairing containing at least one chemical modification such that it is not naturally occurring. A typical nucleobase polymer is a nucleic acid, RNA, DNA, or chemically modified form thereof. A nucleobase polymer may contain DNA or RNA or a combination of DNA or RNA nucleotides or may be single or double stranded or both, e.g., they may contain overhangs, hairpins, bends, and the like. Nucleobase polymers may contain naturally occurring or synthetically modified bases and backbones.

With regard to the nucleobases, it is contemplated that the term encompasses isobases, otherwise known as modified bases, which may be isoelectronic or have other substitutes configured to mimic naturally occurring hydrogen bonding base-pairs. Examples of nucleotides with modified adenosine or guanosine include, but are not limited to, hypoxanthine, xanthine, and 7-methylguanine.

Examples of nucleotides with modified cytidine, thymidine, or uridine include 5,6-dihydrouracil, 5-methylcytosine, 5-hydroxymethylcytosine. Contemplated isobases include 2'-deoxy-5-methylisocytidine (iC) and 2'-deoxy-isoguanosine (iG) (see U.S. Pat. Nos. 6,001,983; 6,037,120; 6,617,106; and 6,977,161 each of which is incorporated herein by reference in its entirety).

Within any of the nucleotide sequences, U may be substituted for T, or T may be substituted for U. U is one of the four nucleobases in the nucleic acid RNA. In DNA, the uracil (U) nucleobase is replaced by thymine (T). Uracil is a demethylated form of thymine. Thus, from a structural standpoint natural RNA is distinct from DNA due to the presence of a 2' hydroxy on the ribose unit and demethylated thymine bases.

ASOs may be chemically modified, e.g., within the sugar backbone or on the 5' or 3' ends. The ASOs comprising RNA can be modified, for example, with 2'-amino, 2'-O-allyl, 2'-fluoro, 2'-O-methyl, 2'-methyl, 2'-H of the ribose ring. The ASOs comprising either RNA or DNA can be modified, for example, with a locked nucleic acid. Locked nucleic acid (LNA) refers to oligonucleotides that contain one or more nucleobases in which an extra methylene bridge fixes the confirmation sugar moiety, e.g., in the C3'-endo (beta-D-LNA) or C2'-endo (alpha-L-LNA) conformation of ribose. Using locked nucleic acids within a nucleobase polymer typically increases the specific binding between a double stranded complex. In certain aspects, the nucleobase polymer comprises locked monomers of 1-(hydroxymethyl)-2,5-dioxabicyclo[2.2.1]heptan-7-ol or phosphorodiamidate morpholino oligomers (PMO).

The term “ASO that hybridizes” refers to a molecule capable of hybridizing to a single-stranded nucleic acid target. The nucleobase polymer may target, e.g., a sequence that is, or is the reverse complement of, more than 7, 8, 9, 10, 11, 12, 13, 14, 15, 20, or more nucleotides or nucleobases or continuous nucleotide nucleobases of nucleic acids associated with an ELAVL3 CE, e.g., SEQ ID NOs: 2-9 (DNA) and 11-18 (RNA). The nucleobase polymer may be a single stranded nucleic acid or analog containing a sufficiently small number of mismatches, additions, or deletions as long as the probe retains the ability to bind to the target. The nucleobase polymer may be the single stranded tail of a double stranded nucleic acid. The nucleobase polymer may be a part of a loop structure or single stranded tail of a hairpin structure. In certain aspects, the nucleobase polymer may be less than 500, 200, 100, 50, or 25 nucleotides or nucleobases. In certain aspects, the ASO is greater than 5, 10, 15, or 20 nucleotides or nucleobases but less than 100, 50, or 25.

The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. In certain aspects, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position.

ASOs and their Modifications

In one aspect, ASOs are provided that bind nucleic acids encoding CEs, thereby suppressing or preventing cryptic splicing of ELAVL3 RNA. In certain aspects, the ASOs decrease cellular levels of or expression of ELAVL3 CE nucleic acids and increase or restore functional ELAVL3 protein expression excluding CE peptide sequences. In some aspects, the ASOs are useful in treating or preventing TDP-43 related neurodegenerative or neurological diseases or conditions relating thereto.

DNA:

In certain aspects, ASOs are provided that specifically bind ELAVL3 DNA or RNA (e.g. pre-mRNA, mRNA, or nascent RNA) sequence(s) coding for a CE, thereby suppressing or preventing inclusion of a CE in ELAVL3 RNA transcripts. In certain aspects, ASOs are provided in the form of DNA that specifically binds ELAVL3 CE DNA or RNA sequences, thereby suppressing or preventing inclusion of an abortive or altered ELAVL3 sequence.

In certain aspects, the ASOs hybridize with ELAVL3 CE DNA or RNA. In certain aspects, the ASOs specifically bind/hybridize with the DNA of the ELAVL3 CE having the following sequence:

```
                                           (SEQ ID NO: 1)
GTGCATGTGACACTGTGACTCCGGCTGTGACCTGATGGGGCCTCAGGGAT

GCGTCTGGCTCTGGCAGGATGTTTGTGTGTCACCGCGATGTTGTGTGGGT

GTGTCTACCTGTGCCCTGCTCTGAGGGATTGAGTGTGATATCGTGTGTTT

GTGCTGCGCTGTGATGG
```

In certain aspects, the ASOs specifically bind/hybridize with the 5' end of the ELAVL3 DNA having SEQ ID NO: 1. In certain aspects, the ASO comprises the DNA sequence AGTCACAGTGTCACATGCAC (SEQ ID NO: 2) or a segment of five contiguous nucleotides thereof. In certain aspects, the ASO comprises the DNA sequence GTCACATGCACCTGTCAAAT (SEQ ID NO: 3; SpAcc01) or a segment of five contiguous nucleotides thereof. In certain aspects, the ASO comprises the DNA sequence GTCACATGCAC (SEQ ID NO: 4) or a segment of five contiguous nucleotides thereof. In certain aspects, the ASO comprises the DNA sequence ACCACATACCCATCACAGCG (SEQ ID NO: 5; SpDon01) or a segment of five contiguous nucleotides thereof. In certain aspects, the ASO comprises the DNA sequence ACAGCCGGAGTCACAGTGTCA (SEQ ID NO: 6; STIX-001) or a segment of five contiguous nucleotides thereof. In certain aspects, the ASO comprises the DNA sequence CCATCAGGTCACAGCCGGAGTCA (SEQ ID NO: 7; STIX-002) or a segment of five contiguous nucleotides thereof. In certain aspects, the ASO comprises the DNA sequence CCAGACGCATCCCTGAGGCC (SEQ ID NO: 8; STIX-003) or a segment of five contiguous nucleotides thereof. In certain aspects, the ASO comprises the DNA sequence CGCGGTGACACACAAACATC (SEQ ID NO: 9; STIX-004) or a segment of five contiguous nucleotides thereof.

In certain aspects, a binding oligonucleotide and the target DNA or RNA sequence (e.g., the abortive or altered ELAVL3 CE pre-mRNA, mRNA, or nascent RNA) have 100% sequence complementarity. In certain aspects, a binding oligonucleotide may comprise sequence variations, e.g., insertions, deletions, additions, and single point mutations, relative to the target sequence. In certain aspects, a binding oligonucleotide has at least 70% sequence identity or complementarity to the target DNA. In certain aspects, a binding oligonucleotide has at least 70%, 75%, 80%, 85%, 90%, 95%, 97%, 99%, or 100% sequence identity to the target sequence.

In certain aspects, in any of the sequences, U may be T or T may be U. In certain aspects, the ASOs are segments between 5 and 10 contiguous nucleotides in length. In certain aspects, the ASOs are segments between 6 and 11 contiguous nucleotides in length. In certain aspects, the ASOs are segments between 7 and 12 contiguous nucleotides in length. In certain aspects, the ASOs are segments between 8 and 13 contiguous nucleotides in length. In certain aspects, the ASOs are segments between 9 and 14 contiguous nucleotides in length. In certain aspects, the ASOs are segments between 10 and 15 contiguous nucleotides in length. In certain aspects, the ASOs are segments between 10 and 20 contiguous nucleotides in length. In certain aspects, the ASOs are segments between 12 and 25 contiguous nucleotides in length. In certain aspects, the ASOs are 20 contiguous nucleotides. In certain aspects, the ASOs are 21 contiguous nucleotides.

In some aspects, the ASOs may be of any size and/or chemical composition sufficient to target the ELAVL3 CE DNA or RNA. In certain aspects, the ASOs are between about 5-300 contiguous nucleotides or modified nucleotides. In certain aspects, the ASOs are between about 5-8, 5-10, 5-15, 8-20, 8-25, 10-100, 15-85, 20-70, 25-55, or 30-40 contiguous nucleotides or modified nucleotides. In certain aspects, the ASOs are between about 15-35, 15-20, 20-25, 25-30, or 30-35 contiguous nucleotides or modified nucleotides.

In certain aspects, the nucleic acid can be any form of interfering DNA that targets ELAVL3 CE DNA or RNA sequences or expression, e.g., short interfering double stranded DNA, 15-23 or 10-25 contiguous nucleobases in length, or hairpins having 20-50 nucleobases in length, wherein the double stranded portion of the hairpin comprises a CE sequence.

In certain aspects, the ASOs comprise deoxyribose sugar modifications wherein the sugar-phosphate backbone of the DNA sequence may comprise one or more of: LNAs such as 1-(hydroxymethyl)-2,5-dioxabicyclo[2.2.1]heptan-7-ol, α-L-locked nucleic acids ("α-L-LNAs") such as 2'-amino-LNA, unlocked nucleic acids ("UNAs") such as 2-(2-hydroxyethoxy)propane-1,3-diol, constrained ethyl bicyclic nucleic acids ("cEt BNAs") such as 2'-0,4'-C-(ethylmethylene) bridged nucleic acid, ethylene-bridged nucleic acids ("ENAs") such as 2'-0,4'-C-ethylene bridged nucleic acid, propylene-bridged nucleic acids (PrNAs), deoxyribose, 2',4'-C methylene bicyclo nucleotide, P-(2-(hydroxymethyl) morpholino)-N,N-dimethylphosphoramidate, morpholin-2-ylmethanol, (2-(hydroxymethyl)morpholino)(piperazin-1-yl)phosphinate, mesyl phosphoramidate, 2'-arabinocytidine, 2'-O-[2-(methylamino)-2-oxoethyl, 2'-deoxy-2'-fluoroarabinocytidine (2'-F-araC), 2'-deoxy-2'-fluororibocytidine, or peptide nucleic acids such as N-(2-aminoethyl) glycine, wherein nucleobases are attached through a methyl carbonyl linker or combinations thereof.

In certain aspects, modified sugar moieties are non-bicyclic modified sugar moieties. In certain aspects, modified sugar moieties are bicyclic or tricyclic sugar moieties. In certain aspects, modified sugar moieties are sugar surrogates. Such sugar surrogates may comprise one or more substitutions corresponding to those of other types of modified sugar moieties.

In some aspects, modified sugar moieties are non-bicyclic modified sugar moieties comprising a furanosyl ring with one or more substituent groups, none of which bridges two atoms of the furanosyl ring to form a bicyclic structure. Such non bridging substituents may be at any position of the furanosyl, including but not limited to substituents at the 2', 4', and/or 5' positions. In certain aspects, one or more non-bridging substituent of non-bicyclic modified sugar moieties is branched.

In certain aspects, modified sugar moieties comprise a substituent that bridges two atoms of the furanosyl ring to form a second ring, resulting in a bicyclic sugar moiety. In certain aspects, the bicyclic sugar moiety comprises a bridge between the 4' and 2' furanose ring atoms.

In certain aspects, an antisense oligonucleotide modification includes LNAs in which the 2'-hydroxyl group is linked to the 3' or 4' carbon atom of the sugar ring thereby forming a bicyclic sugar moiety. The linkage may be a methylene ($—CH_2—$)n group bridging the 2' oxygen atom and the 4' carbon atom, wherein n is 1 or 2.

In certain aspects, modified sugar moieties comprise one or more non bridging sugar substituent and one or more bridging sugar substituent (e g., 5'-substituted and 4'-2'-bridged sugars). Modified oligonucleotides may comprise one or more nucleosides comprising an unmodified nucleobase. In some aspects, modified oligonucleotides comprise one or more nucleosides comprising a modified nucleobase.

In certain aspects, the ASOs may include phosphate modifications wherein the internucleoside linkages of the sugar-phosphate backbone of the DNA sequence may comprise one or more of: phosphodiester, phosphorothioate, phosphorodithioate, methylphosphonate, phosphotriester, phosphoramidate, phosphorodiamidate, piperazine phosphorodiamidate, stereopure phosphorothioate (including defined Rp, Sp, or alternating Rp/Sp stereochemical configurations), methoxypropylphosphonate, thiophosphoramidate, morpholino, amidate carbamate, carboxymethyl, acetamidate, polyamide, sulfonate, sulfonamide, sulfamate, formacetal, thioformacetal, and/or alkylsilyl, substitutions. The phosphodiester linkages of a deoxyribonucleotide may be modified to include at least one nitrogen or sulfur heteroatom. In certain aspects, the phosphoester group connecting to adjacent deoxyribonucleotides is replaced by a modified group, e.g., of phosphorothioate group.

In certain aspects, antisense oligonucleotides are linked together using any internucleoside linkage. The two main classes of internucleoside linking groups are defined by the presence or absence of a phosphorous atom. Representative phosphorus-containing internucleoside linkages include but are not limited to phosphates, which contain a phosphodiester bond ("P═O") (also referred to as unmodified or naturally occurring linkages), phosphotriesters, methylphosphonates, phosphoramidates, N3'→P5' phosphoramidates, mesyl phosphoramidate, phosphorothioates ("P═S"), stereopure phosphorothioates (including defined Rp, Sp, or alternating RP/SP stereochemical configurations), steropure, methoxypropylphosphonate, phosphorodiamidate, piperazine phosphorodiamidate, and phosphorodithioates ("HS-P═S"), boranophosphates, and phorphoroselenoates. Representative non-phosphorus containing internucleoside linking groups include but are not limited to methylenemethylimino ($—CH_2—N(CH_3)—O—CH_2—$), thiodiester, thionocarbamate (—O—C(═O)(NH)—S—); siloxane (—O-Sith-O—); and N,N'-dimethylhydrazine ($—CH_2—N(CH_3)—N(CH_3)—$). Modified internucleoside linkages, compared to naturally occurring phosphate linkages, can be used to alter, typically increase, nuclease resistance of the oligonucleotide. In certain aspects, internucleoside linkages having a chiral atom can be prepared as a racemic mixture or as separate enantiomers.

In certain aspects, the ASOs may include base modifications, e.g., 5-methyl-cytosine, 5-methyluridine, uracil and 5-(1-propynyl)uracil as parts of 2'-deoxynucleotides. In certain aspects, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain aspects, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine, 2-thiocytosine, 5-propyny-uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyl adenine, 2-N-isobutyrylguanine, 4-N-benzoylcytosine, 4-N-benzoyluracil, 5-methyl 4-N-benzoylcytosine, 5-methyl 4-N-benzoyluracil, N4-acetylcytidine, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one, and 9-(2-aminoethoxy)-1,3-diazaphenoxazine-2-one (G-clamp). Modified nucleobases may also include those in which the purine or pyrimidine base is replaced with other heterocycles, for example 7-deazaadenine, 7-deazaguanosine, 2-aminopyridine, and 2-pyridone.

In certain aspects, the ASOs may include at least one modified nucleotide analogue. The nucleotide analogues may be located at positions where the target specific activity, e.g., the splice site selection modulating activity, is not substantially affected, e.g., in a region at the 5'-end and/or the 3'-end of the oligonucleotide molecule. In certain aspects, the ends may be stabilized by incorporating modified nucleotide analogues.

In certain aspects, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain aspects, modified nucleobases are selected from: 2-aminopropyladenine, 2,6-diaminopurine, 5-hydroxymethyl cytosine, xanthine, hypoxanthine, 2-aminoadenine, 6-N-methylguanine, 6-N-methyladenine, 2-propyladenine, 2-thiouracil, inosine, 2-thiothymine, 2-thiocytosine, 5-propyny-uracil, 5-propynylcytosine, 5-thiazole-substituted uracil, 5-phenyltriazol-substituted uracil, 5-phenyltriazol-substituted cytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 5-methyluracil, 7-methylguanine, 7-methyladenine, 2-F-adenine, 2-aminoadenine, 7-deazaguanine, 7-deazaadenine, 3-deazaguanine, 3-deazaadenine, 6-N-benzoyl adenine, 2-N-isobutyrylguanine, 4-N-benzoylcytosine, 4-N-benzoyluracil, 5-methyl 4-N-benzoylcytosine, 5-methyl 4-N-benzoyluracil, N4-acetylcytidine, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one, and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine, and 2-pyridone.

In certain aspects, the ASOs may include one or more (e.g., about 1, 2, 3, 4, 5, 6, 7, 8, 9, 10, or more) G-clamp nucleotides. G-clamp nucleotides belong to the tricyclic phenoxazine class of cytidine analogues, which are characterized by an extended aromatic system that enables additional hydrogen bonding with guanosine residues on the target strand, thereby significantly enhancing duplex stability. A G-clamp is a tricyclic aminoethyl-phenoxazine 2'-deoxy cytidine such as G-clamp: [9-(2-aminoethoxy)-3H-benzo[b]pyrimido[4,5-e][1,4]oxazin-2(10H)-one] nucleobase, guanidino-G-clamp: 1-(2-((2-oxo-2,10-dihydro-3H-benzo[b]pyrimido[4,5-e][1,4]oxazin-9-yl)oxy) ethyl)guanidine nucleobase, i-clamp: 8-(3-aminopropoxy)-3H-benzo [b]pyrimido[4,5-e][1,4]oxazin-2(10H)-one nucleobase, or analogues thereof.

In certain aspects, the ASOs may include one or more 5' and/or a 3'-cap structure. A "cap structure" refers to chemical modifications that have been incorporated at either terminus of the oligonucleotide. See, for example, Matulic-Adamic et al., U.S. Pat. No. 5,998,203, which is incorporated herein by reference in its entirety. These terminal modifications protect the nucleic acid molecule from exonuclease degradation. The cap may be present at the 5'-terminus (5'-cap) or at the 3'-terminal (3'-cap) or may be present on both termini. In non-limiting examples, the 5'-cap includes, but is not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; 5'-vinyl phosphonate; 5'-C-methyl modification; or a bridging or non-bridging methylphosphonate moiety.

In certain aspects, the ASOs may be modified to contain a 3' end thiol group for direct absorption on conjugation to metal, gold, or silver surfaces and particles. Oligonucleotides may be synthesized (e.g., certain modified oligonucleotides or portions of oligonucleotides) using protocols known in the art, such as, for example, described in U.S. Pat. No. 6,001,311, which is incorporated herein by reference in its entirety. The synthesis of oligonucleotides makes use of common nucleic acid protecting and coupling groups, such as dimethoxytrityl at the 5'-end and phosphoramidites at the 3'-end.

In certain aspects, the ASOs are single or double stranded DNA. In certain aspects, the ASOs are 3' end capped with one, two, or more thymidine nucleotides and/or 5' end polyphosphorylated, e.g., di-phosphate, tri-phosphate.

In certain aspects, constructs may be purified by gel electrophoresis using general methods or may be purified by high pressure liquid chromatography and re-suspended in water.

In certain aspects, antibody-oligonucleotide conjugates are contemplated, such as, for example, an ASO tagged to an antibody or scFv to a transferrin receptor or CD98.

In certain aspects, recombinant vectors are provided, the recombinant vectors comprising a nucleic acid encoding ELAVL3 CE sequences in operable combination with heterologous promoters. In certain aspects, the sequences are contained in one or more recombinant vectors encoding the sequences in operable combination with a heterologous promoter.

RNA:

In certain aspects, ASOs are provided that specifically bind ELAVL3 DNA or RNA (e.g. pre-mRNA, mRNA, or nascent RNA) sequence(s) coding for a CE, thereby suppressing or preventing inclusion of a CE in ELAVL3 RNA transcripts. In certain aspects, ASOs are provided in the form of RNA that specifically bind ELAVL3 CE DNA or RNA sequences, thereby suppressing or preventing inclusion of an abortive or altered ELAVL3 sequence.

In certain aspects, the ASOs hybridize with ELAVL3 CE DNA or RNA encoding pre-mRNA or mRNA or expressing pre-mRNA, mRNA, or nascent RNA. In certain aspects, the ASOs specifically bind/hybridize with the RNA of the ELAVL3 CE having the following sequence:

```
                                        (SEQ ID NO: 10)
GUGCAUGUGACACUGUGACUCCGGCUGUGACCUGAUGGGGCCUCAGGGAU

GCGUCUGGCUCUGGCAGGAUGUUUGUGUGUCACCGCGAUGUUGUGUGGGU

GUGUCUACCUGUGCCCUGCUCUGAGGGAUUGAGUGUGAUAUCGUGUGUUU

GUGCUGCGCUGUGAUGG
```

In certain aspects, the ASOs specifically bind/hybridize with the 5' end of the ELAVL3 RNA having SEQ ID NO. 10. In certain aspects, the ASO comprises the RNA sequence AGUCACAGUGUCACAUGCAC (SEQ ID NO: 11) or a segment of five contiguous nucleotides thereof. In certain aspects, the ASO comprises the RNA sequence GUCACAUGCACCUGUCAAAU (SEQ ID NO: 12; SpAcc01) or a segment of five contiguous nucleotides thereof. In certain aspects, the ASO comprises the RNA sequence GUCA-CAUGCAC (SEQ ID NO: 13) or a segment of five contiguous nucleotides thereof. In certain aspects, the ASO comprises the RNA sequence ACCACAUACCCAU-CACAGCG (SEQ ID NO: 14; SpDon01) or a segment of five contiguous nucleotides thereof. In certain aspects, the ASO comprises the RNA sequence ACAGCCGGAGU-CACAGUGUCA (SEQ ID NO: 15; STIX-001) or a segment of five contiguous nucleotides thereof. In certain aspects, the ASO comprises the RNA sequence CCAUCAGGU-CACAGCCGGAGUCA (SEQ ID NO: 16; STIX-002) or a segment of five contiguous nucleotides thereof. In certain aspects, the ASO comprises the RNA sequence CCAGACG-CAUCCCUGAGGCC (SEQ ID NO: 17; STIX-003) or a segment of five contiguous nucleotides thereof. In certain aspects, the ASO comprises the RNA sequence CGCG-GUGACACACAAACAUC (SEQ ID NO: 18; STIX-004) or a segment of five contiguous nucleotides thereof.

In certain aspects, a binding oligonucleotide and the target DNA or RNA sequence (e.g., the abortive or altered ELAVL3 CE pre-mRNA, mRNA, or nascent RNA) have 100% sequence complementarity. In certain aspects, a binding oligonucleotide may comprise sequence variations, e.g., insertions, deletions, additions, and single point mutations, relative to the target sequence. In certain aspects, a binding oligonucleotide has at least 70% sequence identity or complementarity to the target RNA (e.g., ELAVL3 mRNA, pre-mRNA, or nascent RNA). In certain aspects, a binding oligonucleotide has at least 70%, 75%, 80%, 85%, 90%, 95%, 97%, 99%, or 100% sequence identity to the target sequence.

In certain aspects, in any of the sequences, U may be T or T may be U. In certain aspects, the ASOs are segments between 5 and 10 contiguous nucleotides in length. In certain aspects, the ASOs are segments between 6 and 11 contiguous nucleotides in length. In certain aspects, the ASOs are segments between 7 and 12 contiguous nucleotides in length. In certain aspects, the ASOs are segments between 8 and 13 contiguous nucleotides in length. In certain aspects, the ASOs are segments between 9 and 14 contiguous nucleotides in length. In certain aspects, the ASOs are segments between 10 and 15 contiguous nucleotides in length. In certain aspects, the ASOs are segments between 10 and 20 contiguous nucleotides in length. In certain aspects, the ASOs are segments between 12 and 25 contiguous nucleotides in length. In certain aspects, the ASOs are 20 contiguous nucleotides. In certain aspects, the ASOs are 21 contiguous nucleotides.

In some aspects, the ASOs may be of any size and/or chemical composition sufficient to target the ELAVL3 CE DNA or RNA. In certain aspects, the ASOs are between about 5-300 contiguous nucleotides or modified nucleotides. In certain aspects, the ASOs are between about 5-8, 5-10, 5-15, 8-20, 8-25, 10-100, 15-85, 20-70, 25-55, or 30-40 contiguous nucleotides or modified nucleotides. In certain aspects, the ASOs are between about 15-35, 15-20, 20-25, 25-30, or 30-35 contiguous nucleotides or modified nucleotides.

In certain aspects, the nucleic acid can be any form of interfering RNA that targets ELAVL3 CE DNA or RNA sequences or expression, e.g., short interfering double stranded RNA, 15-23 or 10-25 contiguous nucleobases in length, or hairpins 20-50 nucleobases in length, wherein the double stranded portion of the hairpin comprises a CE sequence.

In certain aspects, the ASOs comprise ribose sugar modifications wherein the sugar-phosphate backbone of the RNA sequence may comprise one or more of: LNAs such as 1-(hydroxymethyl)-2,5-dioxabicyclo[2.2.1]heptan-7-ol, α-L-LNAs such as 2'-amino-LNA, UNAs such as 2-(2-hydroxyethoxy)propane-1,3-diol, cEt BNAs such as 2'-0,4'-C-(ethylmethylene) bridged nucleic acid, ENAs such as 2'-0,4'-C-ethylene bridged nucleic acid, PrNAs, ribose, 2',4'-C methylene bicyclo nucleotide, P-(2-(hydroxymethyl) morpholino)-N,N-dimethylphosphoramidate, morpholin-2-ylmethanol, (2-(hydroxymethyl)morpholino) (piperazin-1-yl)phosphinate, mesyl phosphoramidate, 2'-arabinocytidine, 2'-O-[2-(methylamino)-2-oxoethyl], 2'-O-methylribose, 2-O-methoxyethyl ribose, 2'-fluororibose, or peptide nucleic acids such as N-(2-aminoethyl) glycine, wherein nucleobases are attached through a methyl carbonyl linker) or combinations thereof.

In certain aspects, modified sugar moieties are non-bicyclic modified sugar moieties. In certain aspects, modified sugar moieties are bicyclic or tricyclic sugar moieties. In certain aspects, modified sugar moieties are sugar surrogates. Such sugar surrogates may comprise one or more substitutions corresponding to those of other types of modified sugar moieties.

In some aspects, modified sugar moieties are non-bicyclic modified sugar moieties comprising a furanosyl ring with one or more substituent groups, none of which bridges two atoms of the furanosyl ring to form a bicyclic structure. Such non bridging substituents may be at any position of the furanosyl, including but not limited to substituents at the 2', 4', and/or 5' positions. In certain aspects, one or more non-bridging substituent of non-bicyclic modified sugar moieties is branched.

In certain aspects, modified sugar moieties comprise a substituent that bridges two atoms of the furanosyl ring to form a second ring, resulting in a bicyclic sugar moiety. In certain aspects, the bicyclic sugar moiety comprises a bridge between the 4' and 2' furanose ring atoms.

In certain aspects, an antisense oligonucleotide modification includes LNAs in which the 2'-hydroxyl group is linked to the 3' or 4' carbon atom of the sugar ring thereby forming a bicyclic sugar moiety. The linkage may be a methylene $(—CH_2—)n$ group bridging the 2' oxygen atom and the 4' carbon atom, wherein n is 1 or 2.

In certain aspects, modified sugar moieties comprise one or more non bridging sugar substituent and one or more bridging sugar substituent (e g., 5'-substituted and 4'-2'-bridged sugars). Modified oligonucleotides may comprise one or more nucleosides comprising an unmodified nucleobase. In some aspects, modified oligonucleotides comprise one or more nucleosides comprising a modified nucleobase.

In certain aspects, the ASOs may include phosphate modifications wherein the sugar-phosphate backbone of the RNA sequence may comprise one or more of: phosphodiester, phosphorothioate, phosphorodithioate, methylphosphonate, phosphotriester, phosphoramidate, phosphorodiamidate, piperazine phosphorodiamidate, stereopure phosphorothioate (including defined Rp, Sp, or alternating Rp/Sp stereochemical configurations), methoxypropylphosphonate, thiophosphoramidate, morpholino, amidate carbamate, carboxymethyl, acetamidate, polyamide, sulfonate, sulfonamide, sulfamate, formacetal, thioformacetal, and/or alkylsilyl, substitutions. The phosphodiester linkages of a ribonucleotide may be modified to include at least one nitrogen or sulfur heteroatom. In certain aspects, the phosphoester group connecting to adjacent ribonucleotides is replaced by a modified group, e.g., of phosphorothioate group.

In certain aspects, antisense oligonucleotides are linked together using any internucleoside linkage. The two main classes of internucleoside linking groups are defined by the presence or absence of a phosphorous atom. Representative phosphorus-containing internucleoside linkages include but are not limited to phosphates, which contain a phosphodiester bond ("P═O") (also referred to as unmodified or naturally occurring linkages), phosphotriesters, methylphosphonates, phosphoramidates, N3'→P5' phosphoramidates, mesyl phosphoramidate, phosphorothioates ("P═S"), stereopure phosphorothioates (including defined Rp, Sp, or alternating RP/SP stereochemical configurations), steropure, methoxypropylphosphonate, phosphorodiamidate, piperazine phosphorodiamidate, and phosphorodithioates ("HS—P═S"), boranophosphates, and phorphoroselenoates. Representative non-phosphorus containing internucleoside linking groups include but are not limited to methylenemethylimino (—$CH_2$—N($CH_3$)—O—$CH_2$—), thiodiester, thionocarbamate (—O—C(═O)(NH)—S—); siloxane (—O-Sith-O—); and N,N'-dimethylhydrazine (—$CH_2$—N($CH_3$)—N($CH_3$)—). Modified internucleoside linkages, compared to naturally occurring phosphate linkages, can be used to alter, typically increase, nuclease resistance of the oligonucleotide. In certain aspects, internucleoside linkages having a chiral atom can be prepared as a racemic mixture or as separate enantiomers.

In certain aspects, the ASOs may include sugar- and/or backbone-modified ribonucleotides (i.e., include modifications to the phosphate-sugar backbone). For example, the phosphodiester linkages of a ribonucleotide may be modified to include at least one nitrogen or sulfur heteroatom. In certain aspects, the phosphoester group connecting to adjacent ribonucleotides is replaced by a modified group, e.g., of phosphorothioate group. In certain aspects (in the sugar-modified ribonucleotides), the 2' OH-group is replaced by a group selected from H, OR, R, halo, SH, SR, NH2, NHR, $NR^2$ or ON, wherein R is Ci-Ce alkyl, alkenyl or alkynyl and halo is F, Cl, Br, or I.

In certain aspects, the ASOs may include base modifications. In certain aspects, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain aspects, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine, 2-thiocytosine, 5-propyny-uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyl adenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one, and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine, and 2-pyridone.

In certain aspects, the ASOs may include at least one modified nucleotide analogue. The nucleotide analogues may be located at positions where the target specific activity, e.g., the splice site selection modulating activity, is not substantially affected, e.g., in a region at the 5'-end and/or the 3'-end of the oligonucleotide molecule. In certain aspects, the ends may be stabilized by incorporating modified nucleotide analogues.

In certain aspects, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain aspects, modified nucleobases are selected from: 2-aminopropyladenine, 2,6-diaminopurine, 5-hydroxymethyl cytosine, xanthine, hypoxanthine, inosine, 2-aminoadenine, 6-N-methylguanine, 6-N-methyladenine, 2-propyladenine, 2-thiouracil, 2-thiothymine, 2-thiocytosine, 5-propyny-uracil, 5-propynylcytosine, 5-thiazole-substituted uracil, 5-phenyltriazol-substituted uracil, 5-phenyltriazol-substituted cytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 5-methyluracil, 7-methylguanine, 7-methyladenine, 2-F-adenine, 2-aminoadenine, 7-deazaguanine, 7-deazaadenine, 3-deazaguanine, 3-deazaadenine, 6-N-benzoyl adenine, 2-N-isobutyrylguanine, 4-N-benzoylcytosine, 4-N-benzoyluracil, 5-methyl 4-N-benzoylcytosine, 5-methyl 4-N-benzoyluracil, N4-acetylcytidine, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one, and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine, and 2-pyridone.

Also contemplated are nucleobase-modified ribonucleotides, i.e., ribonucleotides, containing at least one non-naturally occurring nucleobase instead of a naturally occurring nucleobase. Examples of modified nucleobases include, but are not limited to, uridine and/or cytidine modifications at the 5-position, e.g., 5-(2-amino)propyl uridine, 5-bromo uridine; 5-methyluridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine; inosine ribonucleotides; N1-methylpseudouridine; 2,6-diaminopurine riboside; and N4-acetylcytidine.

In certain aspects, the ASOs may include one or more (e.g., about 1, 2, 3, 4, 5, 6, 7, 8, 9, 10, or more) G-clamp nucleotides. G-clamp nucleotides belong to the tricyclic phenoxazine class of cytidine analogues, which are characterized by an extended aromatic system that enables additional hydrogen bonding with guanosine residues on the target strand, thereby significantly enhancing duplex stability. A G-clamp is a tricyclic aminoethyl-phenoxazine 2'-deoxy cytidine such as G-clamp: [9-(2-aminoethoxy)-3H-benzo[b]pyrimido[4,5-e][1,4]oxazin-2(10H)-one] nucleobase, guanidino-G-clamp: 1-(2-((2-oxo-2,10-dihydro-3H-benzo[b]pyrimido [4,5-e][1,4]oxazin-9-yl)oxy)ethyl)guanidine nucleobase, i-clamp: 8-(3-aminopropoxy)-3H-benzo [b]pyrimido[4,5-e][1,4]oxazin-2(10H)-one nucleobase, or analogues thereof.

In certain aspects, the ASOs may include one or more 5' and/or a 3'-cap structure. A "cap structure" refers to chemical modifications that have been incorporated at either terminus of the oligonucleotide. See, for example, Adamic et al., U.S. Pat. No. 5,998,203, which is incorporated herein by reference in its entirety. These terminal modifications protect the nucleic acid molecule from exonuclease degradation. The cap may be present at the 5'-terminus (5'-cap) or at the 3'-terminal (3'-cap) or may be present on both termini. In non-limiting examples, the 5'-cap includes, but is not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; 5'-vinyl phosphonate; 5'-C-methyl modification; or a bridging or non-bridging methylphosphonate moiety.

In certain aspects, the ASOs may be modified to contain a 3' end thiol group for direct absorption on conjugation to metal, gold, or silver surfaces and particles. Oligonucleotides may be synthesized (e.g., certain modified oligonucleotides or portions of oligonucleotides) using protocols known in the art, such as, for example, described in U.S. Pat. No. 6,001,311, which is incorporated herein by reference in its entirety. The synthesis of oligonucleotides makes use of common nucleic acid protecting and coupling groups, such as dimethoxytrityl at the 5'-end and phosphoramidites at the 3'-end.

In certain aspects, the ASOs are single or double stranded RNA. In certain aspects, the ASOs are 3' end capped with one, two, or more thymidine nucleotides and/or 5' end polyphosphorylated, e.g., di-phosphate, tri-phosphate.

In certain aspects, the ASOs are modified to enhance stability by modification with nuclease resistant groups, for example, 2'-amino, 2'-C-allyl, 2'-fluoro, 2'-O-methyl, 2'-H ribose groups. In certain aspects, constructs may be purified by gel electrophoresis using general methods or may be purified by high pressure liquid chromatography and re-suspended in water.

In certain aspects, antibody-oligonucleotide conjugates are contemplated, such as, for example, an ASO tagged to an antibody or scFv to a transferrin receptor or CD98.

In certain aspects, recombinant vectors are provided, the recombinant vectors comprising a nucleic acid encoding ELAVL3 CE sequences in operable combination with heterologous promoters. In certain aspects, the sequences to modulate ELAVL3 can be potentially delivered as a siRNA or via viral mediated delivery. In certain aspects, the sequences are contained in one or more recombinant vectors encoding the sequences in operable combination with a heterologous promoter.

Methods for Using the ASOs

In certain aspects, a method is provided for treating, preventing, or reducing the likelihood of a neurodegenerative disease associated with a TDP-pathology or a decline in TDP-43 functionality in neuronal cells in a subject in need thereof, the method comprising administering an effective amount of an ASO or a recombinant vector encoding an ASO or a pharmaceutical composition comprising the same to a subject in need thereof. In some aspects, the ASO hybridizes with the ELAVL3 CE in its DNA or RNA form. In some aspects, the ASO comprises any one of SEQ ID NOs. 2-9.

In other aspects, the ASO hybridizes with the ELAVL3 CE in its DNA or RNA form. In other aspects, the ASO comprises any one of SEQ ID NOs. 11-18

In certain aspects, methods for improving memory or preventing memory loss are provided.

Pharmaceutical Compositions Comprising the ASOs

In certain aspects, pharmaceutical compositions comprising one or more ASO or nucleobase polymer are provided. In certain aspects, the ASO comprises one of SEQ ID NOs. 2-9 or a segment of at least five contiguous nucleotides of thereof. In other aspects, the ASO comprises one of SEQ ID NOs. 11-18 or a segment of at least five contiguous nucleotides of thereof. In certain aspects, this disclosure relates to a pharmaceutical composition comprising a nucleobase polymer, a recombinant vector encoding a nucleobase polymer, or a lipid particle, and a pharmaceutically acceptable excipient. In some aspects, the pharmaceutically acceptable compositions comprise a therapeutically effective amount of one or more of the agents, formulated together with one or more pharmaceutically acceptable carriers (additives), agents, or diluents.

In certain aspects, a pharmaceutical composition comprises an effective amount of an agent (e.g., an ASO) that binds an ELAVL3 mRNA, pre-mRNA, or nascent RNA or DNA sequence coding for a CE, and optionally an effective amount of another active agent, and a pharmaceutically acceptable carrier, diluent, or excipient.

In certain aspects, the pharmaceutical compositions comprising an ASO may be in a lipid formulation. For example, calcium phosphate and diethylaminoethyl (DEAE)-dextran and cationic lipid-based reagents can coat nucleic acids, enabling the formation of lipid complexes for integrating and/or crossing cell membranes. These complexes may be integrated into lipid formations/artificial liposomes. Cationic lipids are typically mixed with neutral lipids such as L-alpha dioleoyl phosphatidylethanolamine to enhance fusion with lipid bilayers. In certain aspects, the pharmaceutical composition comprising an ASO can comprise a delivery vehicle, including liposomes, for administration to a subject; carriers, and diluents and their salts can be present in pharmaceutically acceptable formulations. U.S. Pat. Nos. 6,395,713 and 5,616,490, each of which is incorporated herein by reference in its entirety, further describe general methods for delivery of nucleic acid molecules.

Formulating ASOs within polymeric or lipid nanoparticles (LNPs) is a strategy to prevent degradation. In certain aspects, the ASOs are contained in a particle comprising an ionizable lipid, a neutral helper lipid, cholesterol, and a diffusible polyethylene glycol (PEG)-lipid. In another example, the ASOs are contained in a particle comprising a cyclodextrin polymer.

In certain aspects, the ASOs are encapsulated in liposomes, e.g., by iontophoresis, or by incorporation into other vehicles, such as biodegradable polymers, hydrogels, cyclodextrins (see for example U.S. Pat. Nos. 7,141,540 and 7,060,498, each of which is incorporated herein by reference in its entirety), poly(lactic-co-glycolic)acid (PLGA) and PLCA microspheres (see for example U.S. Pat. No. 6,447,796, which is incorporated herein by reference in its entirety), biodegradable nanocapsules, and bioadhesive microspheres, or by proteinaceous vectors (U.S. Pat. No. 7,067,632, which is incorporated herein by reference in its entirety).

In certain aspects, the ASOs are formulated or complexed with polyethyleneimine and derivatives thereof, such as polyethyleneimine-polyethylene glycol-N-acetylgalactosamine (PEI-PEG-GAL) or polyethyleneimine-polyethylene glycol-tri-N-acetylgalactosamine (PEI-PEG-triGAL) derivatives, poly-L-lysine (PLL), poly lactic-co-glycolic acid (PLGA) nanoparticles, poly beta-amino ester (PBAE) nanoparticles, or cyclodextrin-based nanoparticles. In certain aspects, the ASOs are formulated in lipid-based delivery systems, including liposomes, lipoplexes, lipid nanoparticles (LNPs), or lipid-polymer hybrid nanoparticles, optionally coated with polyethylene glycol (PEG) and further functionalized with targeting moieties. In certain aspects, the ASOs are conjugated to one or more targeting ligands or delivery moieties, including N-acetylgalactosamine (GalNAc) or trivalent GalNAc clusters for asialoglycoprotein receptor (ASGPR)-mediated hepatocyte delivery; cholesterol, fatty acids, or tocopherol for improved hydrophobicity and albumin-mediated tissue distribution; cell-penetrating peptides (CPPs) for enhanced membrane penetration and endosomal escape; transferrin receptor (TfR1)-targeting antibodies or ligands for blood-brain barrier transcytosis and muscle delivery; or antibody-oligonucleotide conjugates (AOCs) for receptor-mediated tissue-specific delivery. In certain aspects, the ASOs are formulated in or on advanced nanoparticle platforms including spherical nucleic acids (SNAs), gold nanoparticles, metal-organic framework (MOF) nanoparticles, or extracellular vesicles and exosomes, or combinations of any of the foregoing.

The pharmaceutical compositions can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, and pastes for application to the tongue; (2) parenteral administration, for example, by subcutaneous, intramuscular, intrathecal, intercranial, intravenous, or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, agents can be implanted into a patient or injected using a drug delivery system.

In certain aspects, the pharmaceutical composition may comprise a pharmaceutical carrier and may comprise further therapeutic agents, respiratory agents, anti-inflammatory agents, and the like.

In certain aspects, a pharmaceutical composition may be in the form of a liquid comprising pH buffering agents and optionally salts and/or saccharide or polysaccharide.

In certain aspects, the pharmaceutically acceptable excipient may be selected from lactose, sucrose, mannitol, triethyl citrate, dextrose, cellulose, methyl cellulose, ethyl cellulose, hydroxyl propyl cellulose, hydroxypropyl methylcellulose, carboxymethylcellulose, croscarmellose sodium, polyvinyl N-pyrrolidone, crospovidone, ethyl cellulose, povidone, methyl and ethyl acrylate copolymer, polyethylene glycol, fatty acid esters of sorbitol, lauryl sulfate, gelatin, glycerin, glyceryl monooleate, silicon dioxide, titanium dioxide, talc, com starch, carnauba wax, stearic acid, sorbic acid, magnesium stearate, calcium stearate, castor oil, mineral oil, calcium phosphate, starch, carboxymethyl ether of starch, iron oxide, triacetin, acacia gum, esters, or salts thereof.

Compositions may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil or sesame oil), and injectable organic esters such as ethyl oleate.

These compositions may also contain preserving, emulsifying, and dispensing agents. Prevention of the action of microorganisms may be controlled by addition of any of various antibacterial, antiviral, and antifungal agents, for example, parabens, chlorobutanol, phenol, sorbic acid, and the like.

Liquid dosage forms may contain inert diluents commonly used in the art, such as water or other solvents, solubilizing agents, and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, sesame oil, glycerol, tetrahydrofurfuryl alcohol, polyethylene glycols, and fatty acid esters of sorbitan or mixtures of these substances, and the like.

In certain aspects, a pharmaceutical composition comprises one or more, two or more, or three or more antisense oligonucleotides. In certain aspects, the two or more antisense oligonucleotides are covalently linked. In certain aspects, the one or more antisense oligonucleotides increase ELAVL3 protein expression.

In certain aspects, the pharmaceutical compositions comprise a multimeric oligonucleotide. The multimeric oligonucleotide comprises one or more sequences. In some aspects, the multimeric oligonucleotide comprises two or more sequences. The multimeric oligonucleotide may comprise multiple copies of a sequence or alternatively may comprise single copies of multiple sequences.

In certain aspects, the pharmaceutical composition further comprises an agent for treating a neurodegenerative disease, an agent for treating a traumatic brain injury, or an agent for treating a proteasome-inhibitor induced neuropathy. In some aspects, the pharmaceutical composition further comprises a JNK inhibitor. In other aspects, the pharmaceutical composition further comprises analgesics, anti-inflammatory drugs, antipyretics, antidepressants, antiepileptics, antihistamines, antimigraine drugs, antimuscarinics, anxiolytics, sedatives, hypnotics, antipsychotics, cardiovascular drugs, corticosteroids, dopaminergics, electrolytes, gastro-intestinal drugs, muscle relaxants, nutritional agents, vitamins, parasympathomimetics, stimulants, anorectics, anti-narcoleptics, aceclofenac, acetaminophen, atomoxetine, almotriptan, alprazolam, amantadine, amcinonide, aminocyclopropane, amitriptyline, amlodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketanserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalycylate, metoclopramide, mianserin, mifepristone, milnacipran, minaprine, mirtazapine, moclobemide, molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprozin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propranolol, propizepine, propoxyphene, protriptyline, quazepam, quinupramine, reboxetine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenazine, thiazides, thioridazine, thiothixene, tiapride, taziprinone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone, and combinations thereof.

Kits Comprising the ASOs

In certain aspects, kits are provided, the kits comprising pharmaceutical compositions comprising an ASO, and optionally another therapeutic agent in the same or a separate pharmaceutical composition or container. The kits may contain a transfer device such a needle, syringe, cannula, capillary tube, pipette, or pipette tip.

In certain aspects, an ASO may be contained in a storage container, dispensing container, sealed, or unsealed, such a vial, bottle, ampule, blister pack, bag (plastic), or box. In certain aspects, other agents may be contained in a storage container, sealed, or unsealed, such a vial, bottle, ampule, blister pack, or box. In certain aspects, the kit further comprises written instructions for using the ASO and optionally other agents for treating and/or preventing a condition in a subject.

EXAMPLES

The following Examples are illustrative and are not intended to limit the scope of the claimed subject matter.

Example 1: Loss of TDP-Expression Results in the Dysregulation of a Significant Number of Proteins, Including ELAVL3 and STMN2 iPS-derived neurons were generated using an established embryoid body differentiation method. Prior to differentiation, iPS colonies were treated with 10 μM ROCK inhibitor Y-27632 (Stem Cell Technologies) for ~1 hour. iPSCs were treated with Accutase (Stem Cell Technologies) for ~8 min to obtain a single cell suspension. Cells were spun out of Accutase and resuspended in N2B27 differentiation medium (1:1 Advanced DMEM-F12/Neurobasal, 1×N2, 1×B27, 0.2% Penstrep, 1×Glutamax, 110 μM β-mercaptoethanol) and seeded in 10 cm Ultra-Low Attachment dishes (Corning) to form embryoid bodies. Cells were maintained as embryoid bodies throughout the differentiation and were fed every 2 days. For the first 2 days, the differentiation medium contained 3 μM CHIR99021 (Stem Cell Technologies), 10 μM SB431542 (Stemgent), 5 μM DMH1 (Tocris), and 10 μM Y-27632 (Tocris). Starting on day 2, 1 μM Retinoic Acid (Sigma) and 500 nM Smoothened Agonist (Millipore) were added to the medium and Y-27632 was removed. On Day 8, CHIR99021 was removed from the medium. On Day 8, SB and DMH1 were removed from the medium. On day 15, 10 μM DAPT (Tocris) was added. 10 ng/mL BDNF (Peprotech) and 10 ng/mL GDNF (Peprotech) were added to the media on day 16. On day 20, embryoid bodies were disassociated to single cells using papain/DNase (Worhtington Bio) and plated on polyornithine/laminin (3.3 g/mL) coated glass coverslips or cell culture plates. Disassociated neurons were maintained in N2B27 maintenance medium (Brainphys, 1×N2, 1×B27 plus, 0.2% Penstrep) supplemented with 10 ng/mL BDNF and 10 ng/mL GDNF. Media was replenished every 2-3 days. On day 6 after plating, cells were transfected with TARDBP siRNA or a non-targeting control siRNA (Dharmacon) at a final concentration of 60 nM. siRNAs and 4 μL of Lipofectamine RNAiMAX were each diluted separately in 250 μL of Opti-MEM, combined, and allowed to complex for 10 minutes at room temperature. The resulting 500 μL siRNA-lipid complexes were added dropwise to each well of a 6-well containing 2 mL of neuron maintenance medium. Cells were incubated at 37° C. in 5% $CO_2$ for 4 hours, after which the medium was replaced with fresh maintenance media. On day 10, total RNA was isolated using a column-based RNA extraction kit with on-column DNase digestion (Zymo). RNA concentration and integrity were assessed prior to library preparation. RNA sequencing was performed by Novogene. Directional mRNA-seq libraries were prepared using the NEBNext Ultra II Directional mRNA Library Prep Kit and sequenced on an Illumina NovaSeq platform to generate paired-end 150 bp reads.

The data shown in FIG. 1 shows that loss of TDP-43 leads to a significant reduction of ELAVL3 expression as a result of the inclusion of the CE into the ELAVL3 transcript, which leads to premature termination of translation. This suggests that ELAVL3 expression is downstream of TDP-43. Expression of STMN2 is affected in a similar way, with inclusion of the STMN2 CE as a result of loss of TDP-43 expression leading to a reduction of STMN2 expression.

Example 2: TDP-43 Plays a Role in ELAVL3 Splicing, and Loss of TDP-43 Leads to an Irregular Splicing Event in ELAVL3

Figure 2:
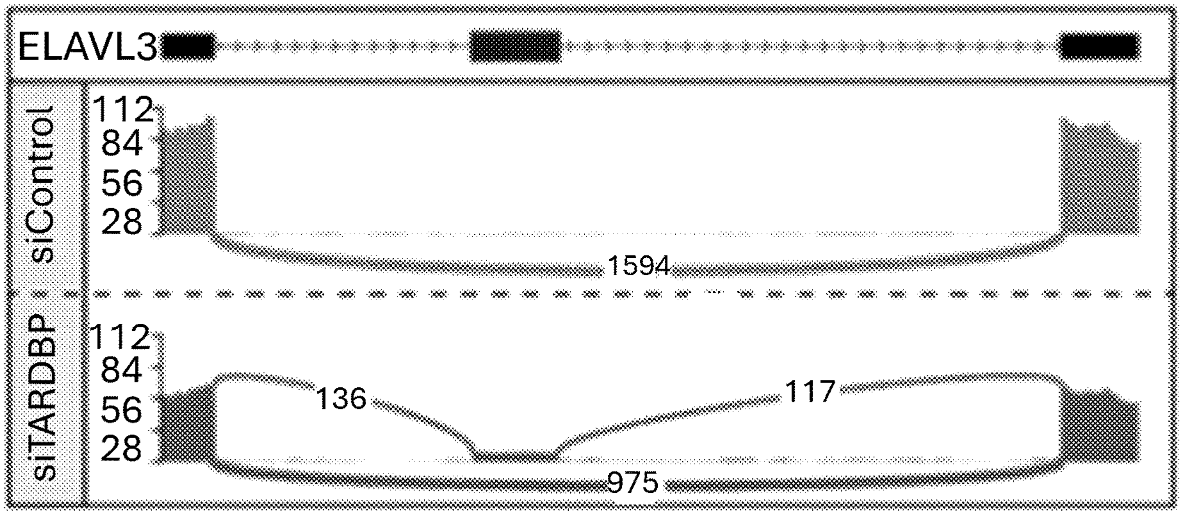
FIG. 2 shows a sashimi plot demonstrating the presence of a CE in ELAVL3 between exon 3 and exon 4 in iPS-derived neurons treated with a siRNA specific to TARDBP to reduce TDP-43 protein levels.

Data from Example 1 was analyzed, and the software rmats2sashimiplot was used to generate FIG. 2. This data shows the inclusion of a CE in ELAVL3 in iPS derived neurons when levels of TDP-43 are reduced using siRNA targeting the TDP-43 transcript. This demonstrates that TDP-43 plays a role in ELAVL3 splicing, and that loss of TDP-43 leads to an irregular splicing event in ELAVL3, which in turn leads to reduced expression of the ELAVL3 protein.

Example 3: Formation of the ELAVL3 CE

Postmortem frontal cortex tissue from an FTLD-TDP case was homogenized in TRIzol using a Bullet Blender. Following chloroform phase separation, the aqueous phase was collected, diluted 1:1 with ethanol, and purified using a column-based RNA cleanup protocol with on-column DNase digestion (Zymo). One microgram of total RNA was reverse transcribed into cDNA using the High-Capacity cDNA Reverse Transcription Kit (ThermoFisher Scientific). One microliter of cDNA was amplified by PCR using Taq polymerase with a forward primer annealing to exon 2 of ELAVL3 and a reverse primer annealing within the CE. RT-PCR products were resolved on a 1% agarose E-Gel (Thermo Fisher Scientific). The PCR band corresponding to the expected amplicon size was excised, gel-purified, and cloned into a TOPO vector. Plasmid inserts were verified by Sanger sequencing performed by a commercial sequencing service (Genewiz).

Figure 3A:
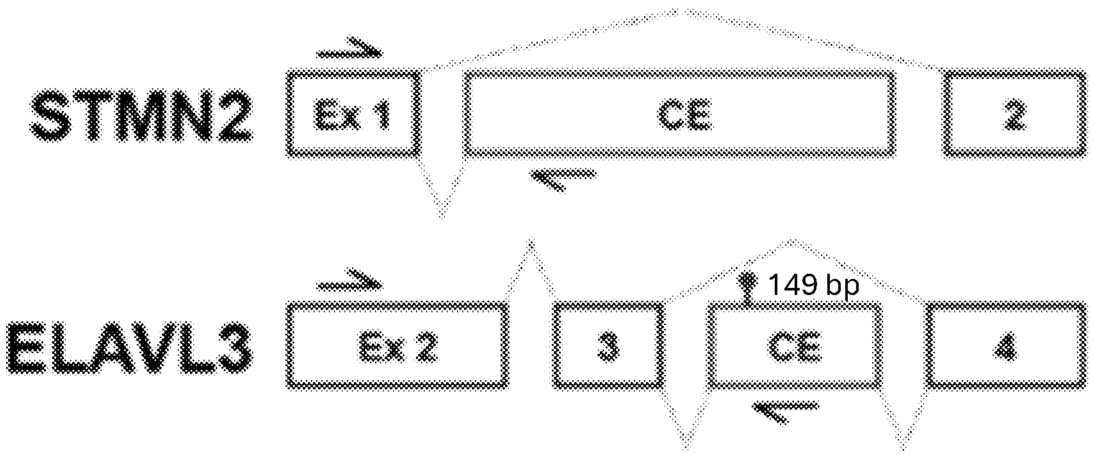
FIG. 3A shows the position of the PCR primers on STMN2 and ELAVL3 that are used to assess presence of the cryptic exon (CE) in those two transcripts.
Figure 3B:
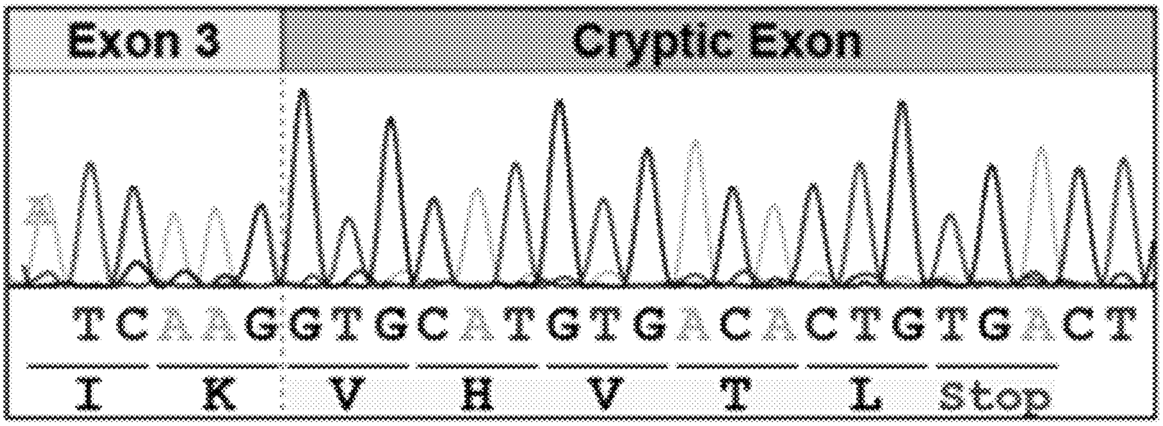
FIG. 3B shows RT-PCR amplification and sequencing of the ELAVL3 CE (SEQ ID NOs. 22 and 23) using the primers shown in FIG. 3A.

RT-PCR amplification of the ELAVL3 CE was performed. FIG. 3A shows the position of the PCR primers on STMN2 and ELAVL3 that are used to assess the presence of the CE in those two transcripts. Sequencing was performed to confirm that the PCR product is indeed derived from the inclusion of the CE in the ELAVL3 transcript. The gene sequence shown in FIG. 3B matches the anticipated sequence of the Exon 3-CE boundary, and the predicted protein sequence shows the premature stop codon introduced by the inclusion of the CE. This experiment confirms that the ELAVL3 transcript containing the CE is indeed formed as anticipated and confirms that the inclusion of the CE can be correctly detected using the PCR set-up described above.

Example 4: ELAVL3 CE is Robustly Detected in the Frontal Cortex of FTLD-TDP Patients Postmortem frontal cortex tissue from non-neurologic controls ("Control") or FTLD-TDP ("FTLD") cases were homogenized in TRIzol using a Bullet Blender. Following chloroform phase separation, the aqueous phase was collected, diluted 1:1 with ethanol, and purified using a column-based RNA cleanup protocol with on-column DNase digestion (Zymo). 1,000 nanograms of RNA were reverse transcribed into cDNA using the High-Capacity cDNA Reverse Transcription Kit (ThermoFisher Scientific), and the resulting cDNA was diluted with 60 μL of nuclease-free water. Quantitative PCR was performed using TaqMan Custom Gene Expression Assays for ELAVL3 CE (ThermoFisher Scientific; Assay ID AP7DWP9) following the manufacturer's protocol. Reactions (20 μL) contained 2 μL diluted cDNA, 1 μL each of 20× target and endogenous control probes, 10 μL of 2×TaqMan Fast Advanced Master Mix, and nuclease-free water, and were run in duplicate in MicroAmp 96-well optical plates (ThermoFisher Scientific; N8010560). Fast cycling qPCR was performed with an initial activation step at 95° C. for 20 s, followed by 40 cycles of 95° C. for 1 s and 60° C. for 20 s. RPLP0 and GAPDH was used as the endogenous control (ThermoFisher Scientific; 4326314E and 4326317E), and relative expression levels were calculated using the comparative Ct (ΔΔCt) method.

Figure 4A:
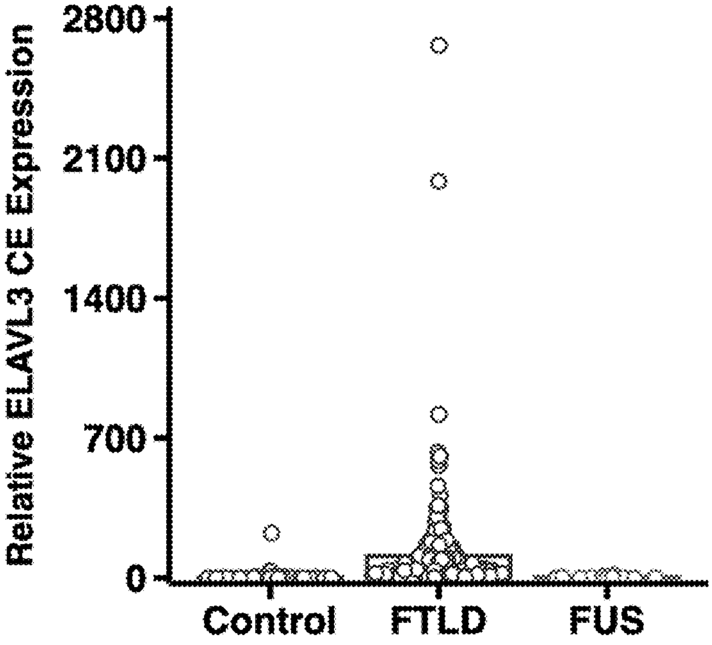
FIG. 4A shows the relative expression of the ELAVL3 CE in the frontal cortex of FTLD-TDP patients compared to control and FTLD-FUS (fused in sarcoma) patients.
Figure 4B:
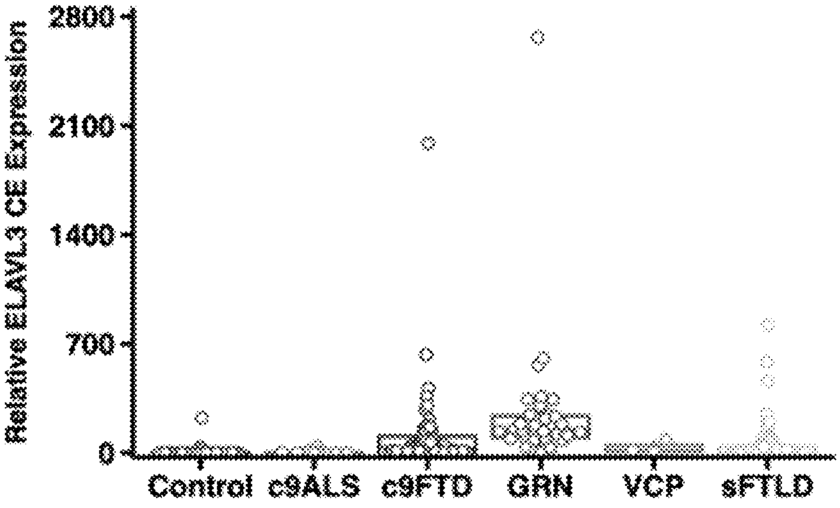
FIG. 4B shows the relative expression of ELAVL3 CE in the frontal cortex of FTLD-TDP patients stratified by genetic status.

FIGS. 4A and 4B show that ELAVL3 CE is robustly detected in the frontal cortex of FTLD-TDP cases. Specifically, FIG. 4A shows the relative expression of ELAVL3 CE in the frontal cortex across control (n=59), FTLD-TDP (n=191), and FTLD-FUS (n=11) cases. FIG. 4B shows the relative expression of ELAVL3 cryptic exon in the frontal cortex of FTLD-TDP cases stratified by genetic status (c9ALS=C9orf72 associated ALS (n=13); c9FTD=C9orf72 associated FTLD(/ALS) (n=53); GRN=FTLD-GRN (GRN mutations) (n=36); VCP=FTLD-VCP (VCP mutations) (n=3); sFTLD=sporadic FTLD-TDP cases (n=99)).

Example 5: ELAVL3 CE is Robustly Detected in the Spinal Cord of ALS Patients

Figure 5:
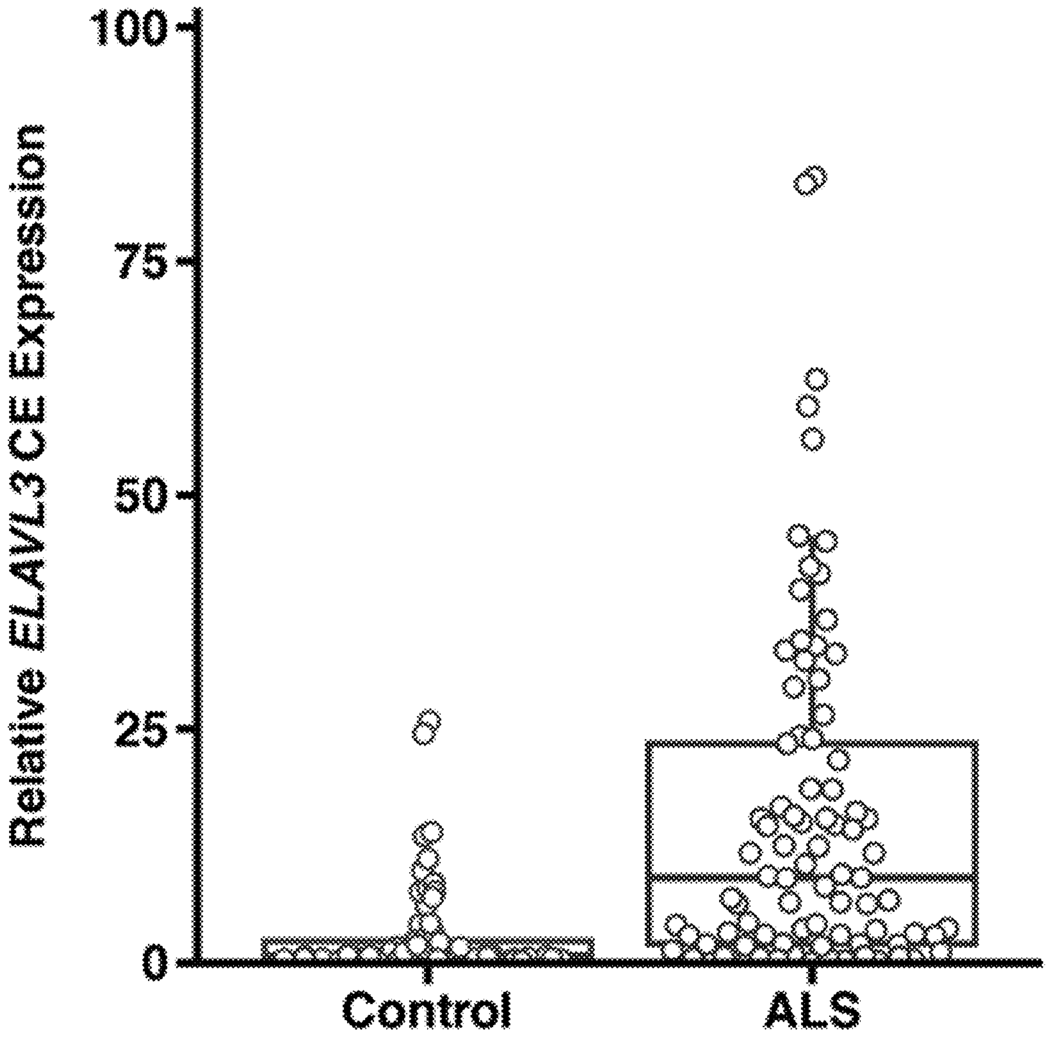
FIG. 5 shows the relative expression of ELAVL3 CE in the spinal cord of ALS patients compared to control patients.

Postmortem spinal cord tissue from non-ALS controls ("Control") or ALS cases were homogenized in TRIzol using a Bullet Blender. Following chloroform phase separation, the aqueous phase was collected, diluted 1:1 with ethanol, and purified using a column-based RNA cleanup protocol with on-column DNase digestion (Zymo). 700 nanograms of RNA were reverse transcribed into cDNA using the High-Capacity cDNA Reverse Transcription Kit (ThermoFisher Scientific), and the resulting cDNA was diluted with 60 μL of nuclease-free water. Quantitative PCR was performed using TaqMan Custom Gene Expression Assays for ELAVL3 CE (ThermoFisher Scientific; Assay ID AP7DWP9) following the manufacturer's protocol. Reactions (20 μL) contained 2 μL diluted cDNA, 1 μL each of 20× target and endogenous control probes, 10 μL of 2×TaqMan Fast Advanced Master Mix, and nuclease-free water, and were run in duplicate in MicroAmp 96-well optical plates (ThermoFisher Scientific; N8010560). Fast cycling qPCR was performed with an initial activation step at 95° C. for 20 s, followed by 40 cycles of 95° C. for 1 s and 60° C. for 20 s. RPLP0 and GAPDH was used as the endogenous control (ThermoFisher Scientific; 4326314E and 4326317E), and relative expression levels were calculated using the comparative Ct (ΔΔCt) method. FIG. 5 shows the relative expression of ELAVL3 CE in the spinal cord of control (n=69) and ALS (n=85) cases and demonstrates that ELAVL3 CE is robustly detected in the spinal cord of ALS cases.

Example 6: Inclusion of the CE in ELAVL3 is a Prominent Feature of FTLD Patients Postmortem frontal cortex tissue from non-neurologic controls ("Control") or FTLD-TDP ("FTLD") cases were homogenized in TRIzol using a Bullet Blender. Following chloroform phase separation, the aqueous phase was collected, diluted 1:1 with ethanol, and purified using a column-based RNA cleanup protocol with on-column DNase digestion (Zymo). 200 ng of purified RNA was used for a custom nCounter Assay (Nanostring) following the manufacture's protocol. One nCounter probe was designed to hybridize across the exon 3-CE junction (P1), and a second probe was designed to hybridize across the exon 3-exon 4 junction (P2). Percent spliced in (PSI) for each sample was calculated as the ratio of P1 counts to the sum of P1 and P2 counts: P1/(P1+P2).

Figure 6:
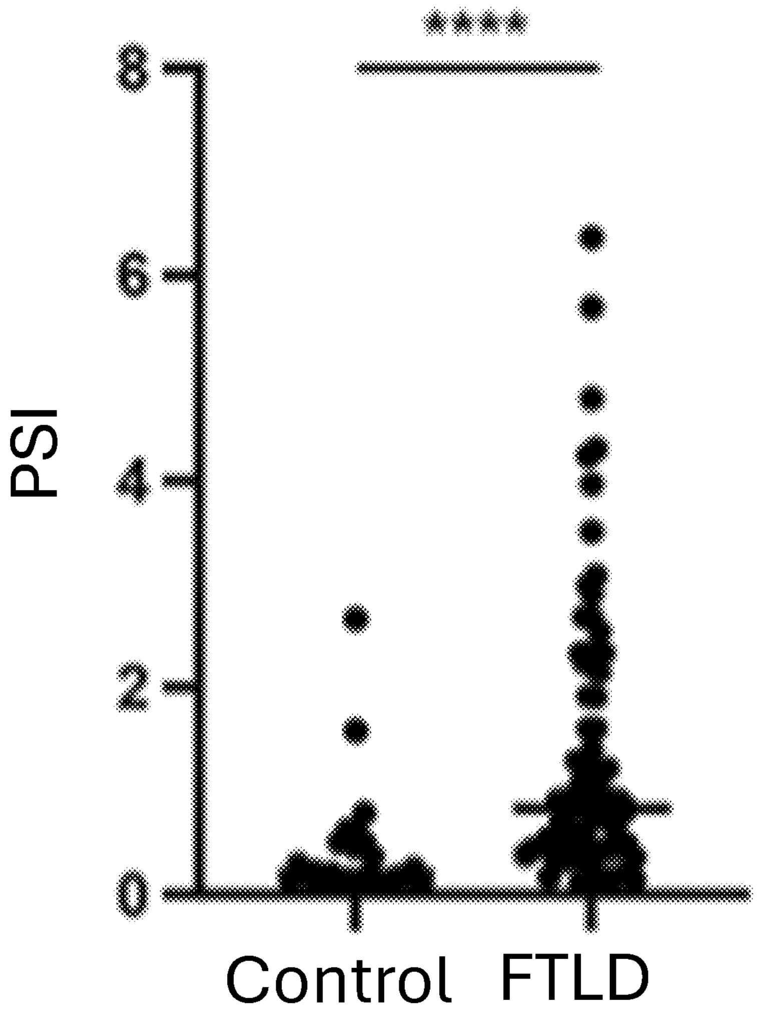
FIG. 6 shows data from a custom Nanostring panel to assess inclusion of the ELAVL3 CE as a percent spliced (PSI) in control and FTD patients.

FIG. 6 shows inclusion of the ELAVL3 CE in control and FTD patients. While only two control patients show significant levels of ELAVL3 transcripts that contain the CE, a large number of FTD patients show significant elevation of ELAVL3 transcripts containing the CE. Inclusion of the CE in ELAVL3 is a prominent feature of FTLD patients. This experimental approach can also be used to select patients with high levels of CE ELAVL3, which would be expected to be more responsive to treatment with ASOs targeting this CE.

Example 7: Design of ELAVL3 ASOs

Figure 7:
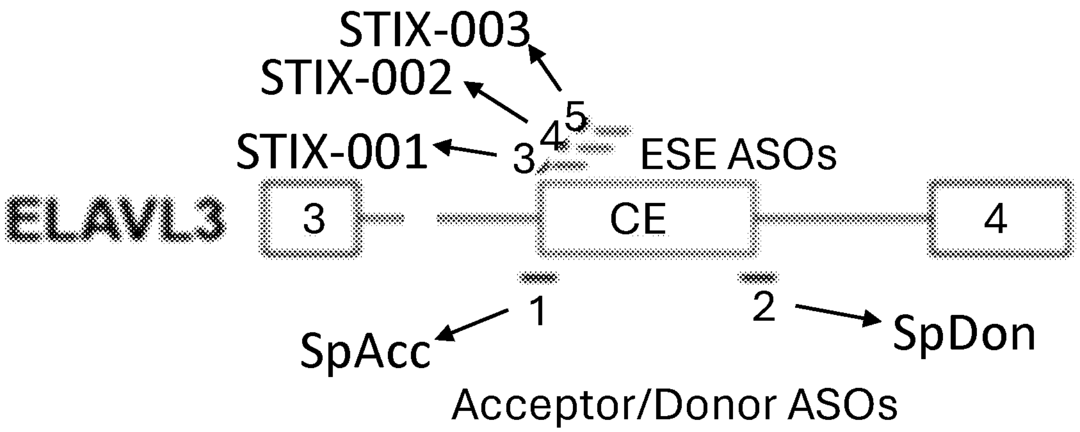
FIG. 7 shows the structure of the ELAVL3 gene between Exon 3 and Exon 4, the position of the CE, and the position of the five ASOs tested. SpAcc (SEQ ID NO. 12) covers the splice acceptor site of the CE, SpDon (SEQ ID NO. 14) covers the splice donor site of the CE, and STIX-001 (SEQ ID NO. 15), STIX-002 (SEQ ID NO. 16), and STIX-003 (SEQ ID NO: 17) are positioned at the 5' end of the ELAVL3 CE.

A series of splice-switching antisense oligonucleotides (ASOs) were designed to target the CE region within the ELAVL3 gene that becomes aberrantly included upon loss of TDP-43 function. The locations of these ASOs are shown in FIG. 7. Two of the optimized ASOs, designated STIX-001 (comprising the nucleobase polymer sequence ACAGCCG-GAGUCACAGUGUCA, SEQ ID NO: 15) and STIX-002 (comprising the nucleobase polymer sequence CCAUCAG-GUCACAGCCGGAGUCA, SEQ ID NO: 16), were developed to bind sequences flanking the CE acceptor, donor, and exonic splicing enhancer (ESE) sites to prevent CE inclusion. Both ASOs were synthesized with phosphorothioate backbones and 2'-O-methoxyethyl (2'-MOE) modifications for nuclease stability and efficient splice modulation.

Example 8: Restoration of ELAVL3 Splicing in Human iNeurons

Figure 8A:
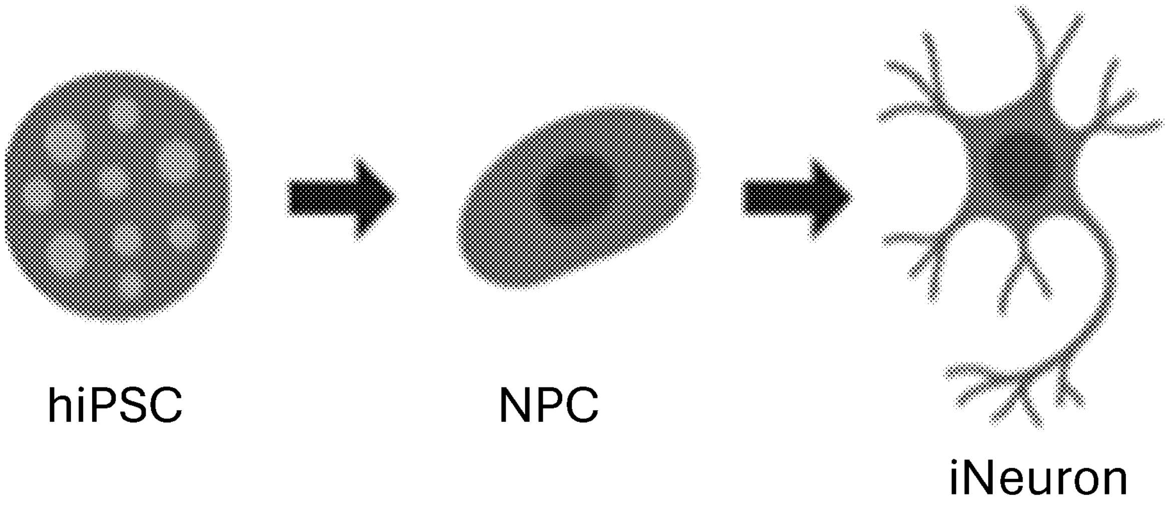
FIG. 8A shows a schematic of differentiation of human induced Pluripotent Stem Cells (hiPSC) through Neuronal Precursor Cells (NPC) to a differentiated neuron (iNeuron).

To establish a cellular model of TDP-43 loss of function, an isogenic KOLF2.1 iPSC line harboring a tetracycline-inducible NGN2 transcription factor was differentiated into cortical neurons (i3Neurons) using an established protocol (Flores et al., dx.doi.org/10.17504/protocols.io.n2bvj3owblk5/v1, which is incorporated by reference herein in its entirety). The schematic is shown in FIG. 8A. iPSCs were dissociated to single cells using Accutase and pelleted at 500×g for 3 minutes. The cell pellet was resuspended in induction medium (DMEM/F12 supplemented with 1×N2, 1× non-essential amino acids, 1×GlutaMAX, and 2 μg/mL doxycycline) containing 50 nM Chroman I and plated onto Matrigel-coated plates at a density of $1\times10^6$ cells per well of a 6-well plate. Cells were replenished daily with fresh induction medium lacking Chroman I for three days.

On day 4, cells were dissociated with Accutase and replated onto poly-ornithine-coated plates, and the medium was switched to neuronal maturation medium (1:1 DMEM/F12:BrainPhys supplemented with 1×N21Max, 10 ng/mL GDNF, 10 ng/mL BDNF, 10 ng/mL NT-3, 1 μg/mL laminin, 2 μg/mL doxycycline, 1 μM 5'-fluoro-2'-deoxyuridine, and 1 μM uridine). Fresh neuronal maturation medium was added on day 7.

On day 10, the medium was replaced with BrainPhys-based neuronal maturation medium (BrainPhys supplemented with 1×N21Max, 10 ng/mL GDNF, 10 ng/mL BDNF, 10 ng/mL NT-3, 1 μg/mL laminin, 2 μg/mL doxycycline, 1 μM 5'-fluoro-2'-deoxyuridine, and 1 μM uridine). Media were replenished every 2-3 days thereafter. On day 15, cells were treated with ACELL siRNAs targeting either a non-targeting scrambled control (Dharmacon D-001910-01-50; Lot #3591923) or TARDBP (Dharmacon E-012394-00-0050; Lot #3591923) at a final concentration of 500 nM, together with either NC5 (a non-targeting control ASO), STIX-001, or STIX-002, at a final concentration of 10 μM. On day 21, total RNA was isolated using a column-based RNA extraction kit with on-column DNase digestion (Zymo). Five hundred nanograms of RNA were reverse transcribed into cDNA using the High-Capacity cDNA Reverse Transcription Kit (ThermoFisher Scientific), and the resulting cDNA was diluted with 40 μL of nuclease-free water. Quantitative PCR was performed using TaqMan Gene Expression Assays for TARDBP (Thermo Fisher Scientific; Hs00606522_ml) and custom TaqMan assays targeting the ELAVL3 CE (ThermoFisher Scientific; Assay ID AP7DWP9) and tSTMN2 CE (Thermo Fisher Scientific; Assay ID APZTKFJ), following the manufacturer's protocol. Reactions (20 μL) contained 2 μL diluted cDNA, 1 μL each of 20× target and endogenous control probes, 10 μL of 2×TaqMan Fast Advanced Master Mix, and nuclease-free water, and were run in duplicate in MicroAmp 96-well optical plates (ThermoFisher Scientific; N8010560). Fast cycling qPCR was performed with an initial activation step at 95° C. for 20 s, followed by 40 cycles of 95° C. for 1 s and 60° C. for 20 s. RPLP0 was used as the endogenous control (ThermoFisher Scientific; 4326314E), and relative expression levels were calculated using the comparative Ct (ΔΔCt) method.

Figure 8B:
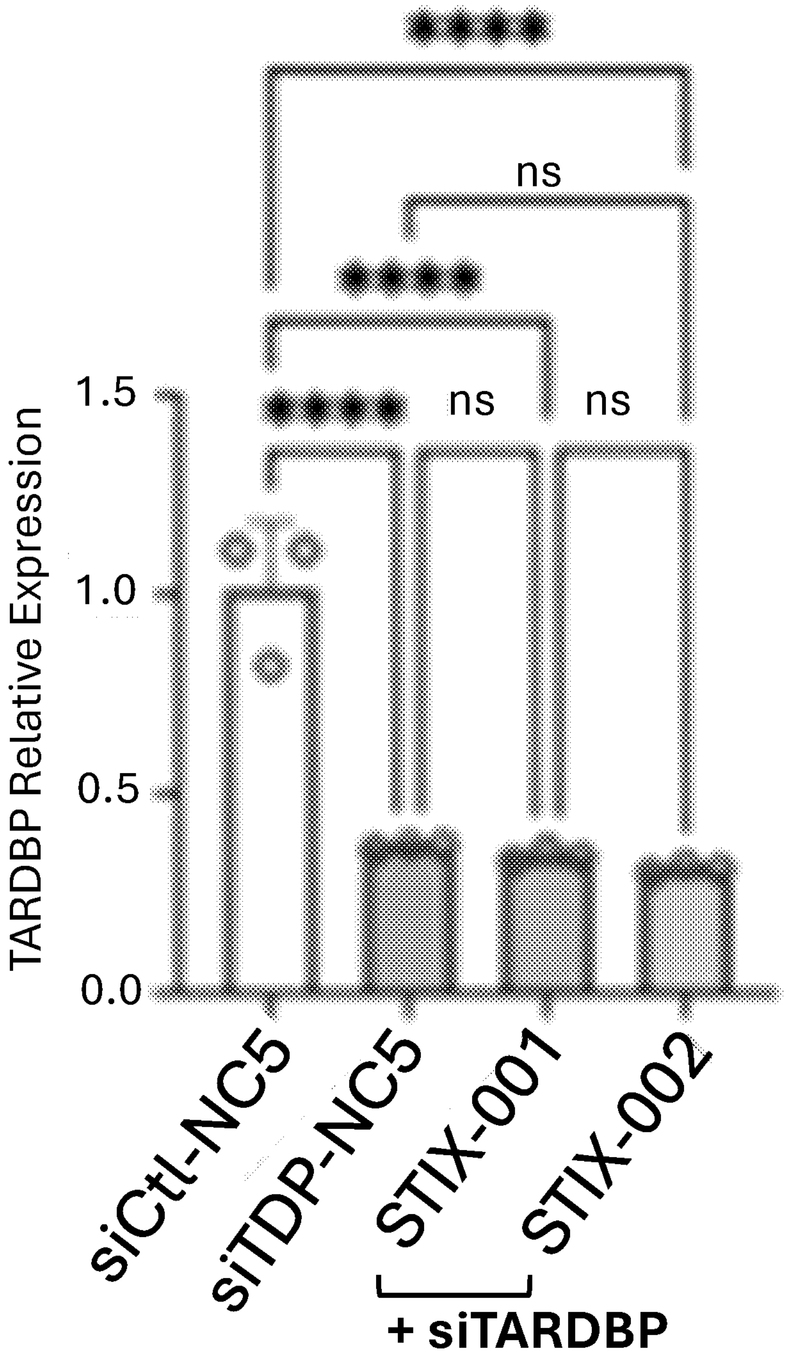
FIGS. 8B-8D show the respective expression level of TARDBP (FIG. 8A), ELAVL3 CE (FIG. 8B), and tSTMN2 (FIG. 8C) in iNeurons after treatment with siCtl-NC5 or siTDP-NC5 with or without STIX-001 or STIX-002.
Figure 8C:
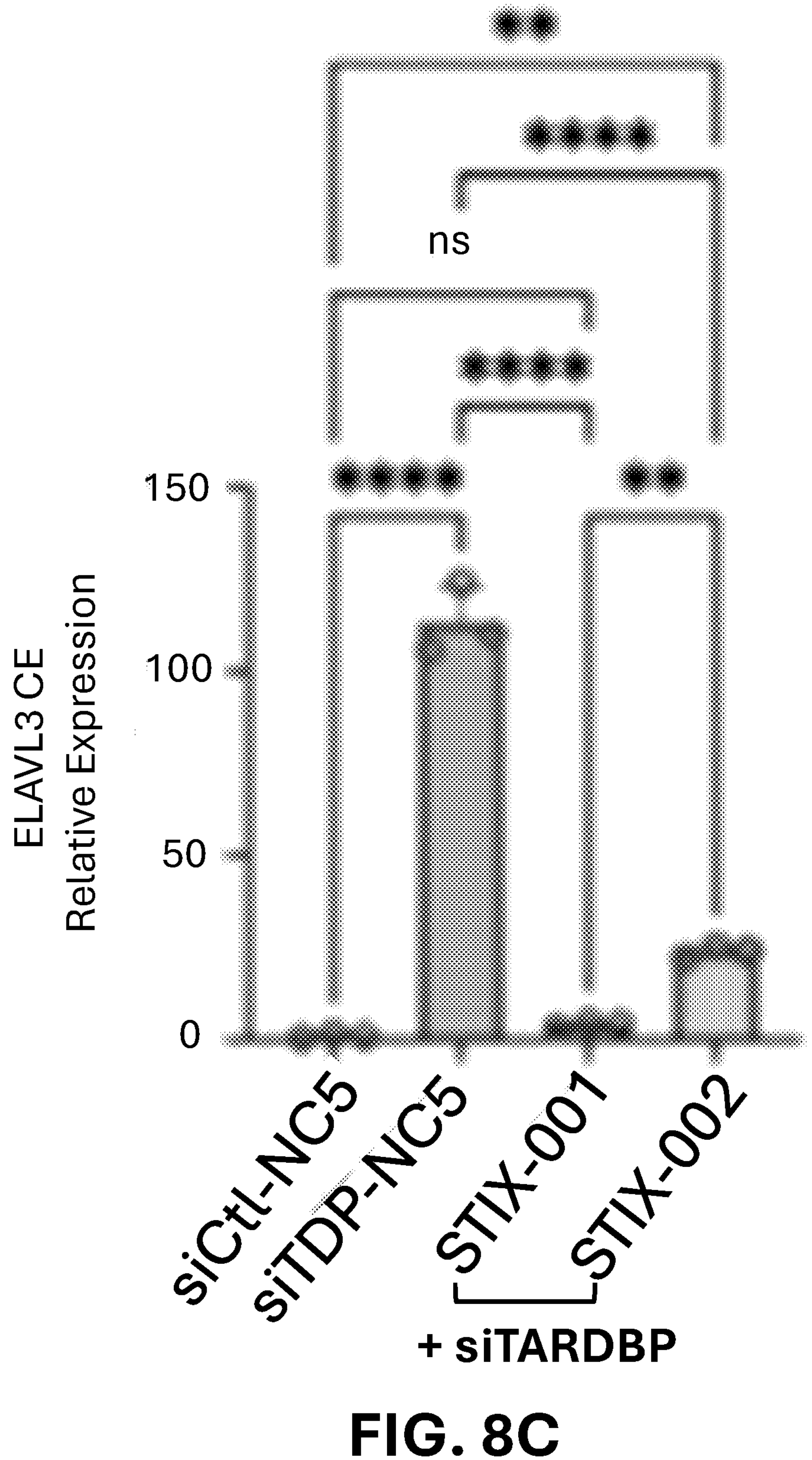
Figure 8D:
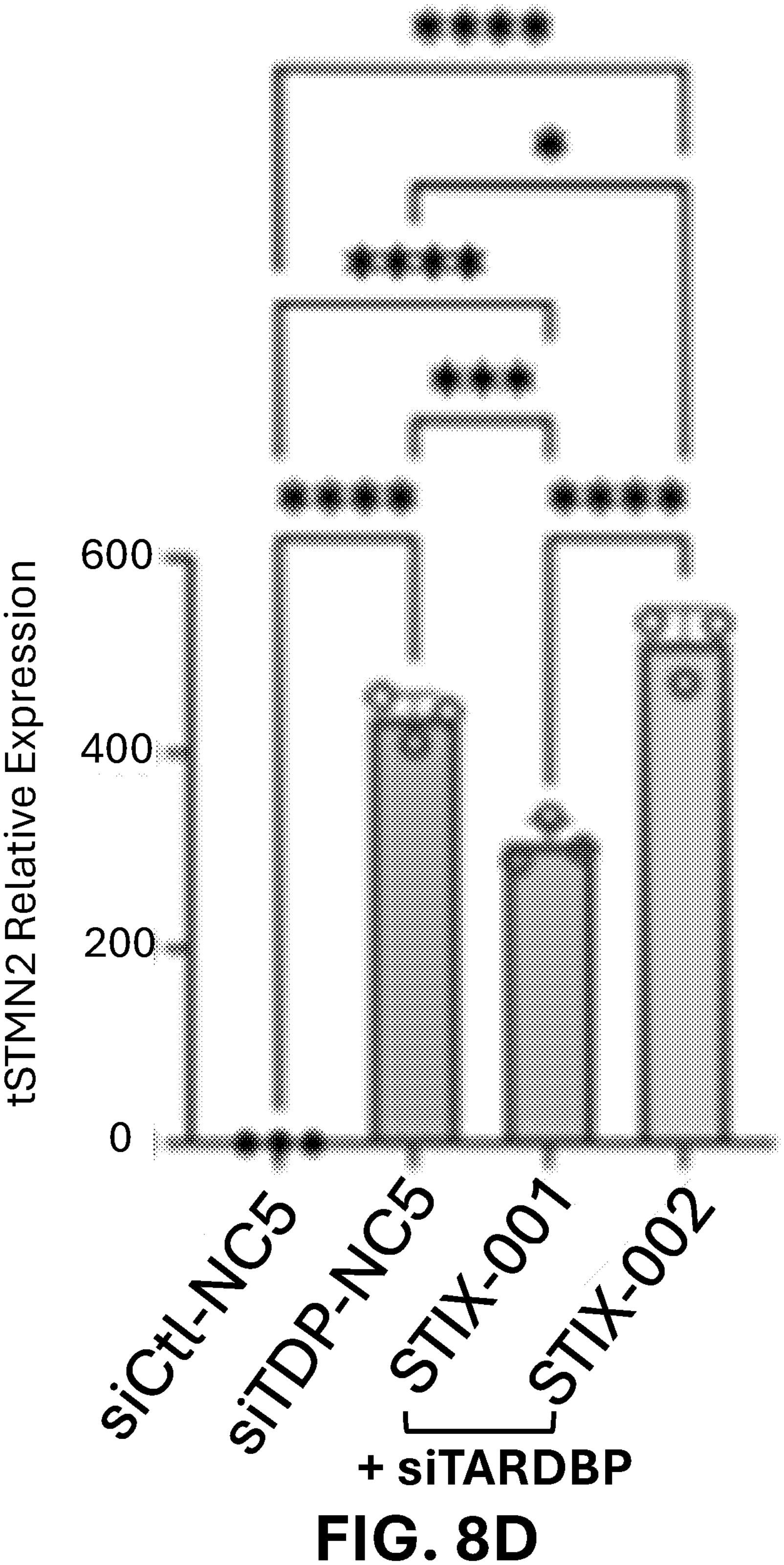

As expected, FIG. 8B demonstrates that treatment of iNeurons with siRNA targeting TDP-43 leads to a reduction of TDP-43 expression levels ("siTDP-NC5"). Treatment with siRNA targeting TDP-43 and either STIX-001 or STIX-002 has no further impact on TDP-43 expression. FIG. 8C shows the levels of CEs in ELAVL3 transcripts as a function of TDP-43 levels. In control iNeurons, the levels of ELAVL3 CE are undetectable. Reduction of TDP-43 expression increases CE inclusion in the ELAVL3 transcript ("siTDP-NC5"). Treatment of iNeurons with siRNA targeting TDP-43 and STIX-001 reduces ELAVL3 CE levels back to control levels. Treatment of iNeurons with siRNA targeting TDP-43 and STIX-002 leads to a significant reduction of ELAVL3 CE levels, but these CE levels remain elevated compared to control cells. Finally, FIG. 8D shows expression levels of a truncated form of STMN2 (tSTMN2), which is expressed due to the inclusion of a CE in the STMN2 transcript by aberrant splicing. In control cells, levels of tSTMN2 are undetectable. Reduction of TDP-43 levels using siRNA targeting the TDP-43 transcript leads to inclusion of a CE in the STMN2 transcript and, as a result, in expression of the tSTMN2 protein. Treatment of the cells with STIX-001 partially rescues this defect induced by reduced TDP-43 expression: tSTMN2 levels in cells treated with TDP-43 siRNA and STIX-001 are significantly lower than in cells treated with TDP-43 siRNA alone, but they are elevated compared to control cells. Treatment of iNeurons with TDP-43 siRNA and STIX-002 does not impact inclusion of the CE in STMN2 and thus expression levels of tSTMN2.

This data shows an increase of CE inclusion in ELAVL3 and STMN2 in cells with TDP-43 knock-down compared to wild-type iPSC-derived human neurons (iNeurons). Treatment of cells with reduced levels of TDP-43 expression with STIX-001, which directly targets the aberrant splicing of ELAVL3 transcripts that leads to the inclusion of CEs, significantly reduces the level of CE inclusion in ELAVL3. In cells treated with STIX-001, the levels of ELAVL3 CE are indistinguishable from control cells. Levels of CE inclusion in STMN2 are partially corrected by STIX-001 but not with STIX-002. Expression of STMN2 transcripts containing CEs remains significantly elevated compared to control even after treatment with STIX-001.

Example 9: STIX-001 Treatment Restores Normal Splicing and Expression in SH-SY5Y Cells SH-SY5Y cells were maintained in growth medium (SH-SY5Y medium) consisting of DMEM/F12 supplemented with 10% fetal bovine serum (FBS), 100 U/mL penicillin, and 100 μg/mL streptomycin at 37° C. in a humidified incubator with 5% $CO_2$. For ASO transfection experiments, cells were seeded in 12-well tissue culture-treated plates at a density of approximately $2.5\times10^5$ cells per well, ~24 hours prior to transfection, to achieve 50-70% confluency at the time of ASO delivery.

For ASO/siRNA co-transfection, the appropriate amounts of ASO (non-targeting NC5 or STIX001-004) and siRNA (non-targeting control or TARDBP) were diluted together in 100 μL of Opti-MEM Reduced Serum Medium to achieve final concentrations of 100 nM each in a 12-well plate (1 mL total volume). Lipofectamine reagent (4 μL per well) was diluted separately in 100 μL of Opti-MEM and combined with the diluted ASO/siRNA mixture (200 μL total volume), followed by incubation at room temperature for 15-20 minutes to allow complex formation. 200 μL of the ASO/siRNA-lipid complexes were added dropwise to each well containing 900 μL of antibiotic-free medium. The TARDBP Smartpool siRNAs target the following sequences in TARDBP: 5'-GGCUCAAGCAUGGAUUCUA-3' (SEQ ID NO. 19), 5'-GUCUCAAGUCAAAUGGAUU-3' (SEQ ID NO. 20), and 5'-GUGUUAAGUGAAAUGAUAC-3' (SEQ ID NO. 21). siRNAs were reconstituted in nuclease-free water to a stock concentration of 20 μM and stored at −20° C. ASOs were diluted in nuclease-free water to a stock concentration of 100 μM and stored at −20° C.

At 72 hours post-transfection, cells were rinsed once with 1×PBS, and total RNA was isolated using a column-based RNA extraction kit with on-column DNase digestion (Zymo). One microgram of RNA was reverse transcribed into cDNA using the High-Capacity cDNA Reverse Transcription Kit (Thermo Fisher Scientific), and the resulting cDNA was diluted with 60 μL of nuclease-free water. Quantitative PCR was performed using custom TaqMan assays targeting ELAVL3 CE (Thermo Fisher Scientific; Assay ID AP7DWP9) and tSTMN2 CE (Thermo Fisher Scientific; Assay ID APZTKFJ), following the manufacturer's protocol. Reactions (20 μL) contained 2 μL diluted cDNA, 1 μL each of 20× target and endogenous control probes, 10 μL of 2×TaqMan Fast Advanced Master Mix, and nuclease-free water, and were run in duplicate in MicroAmp 96-well optical plates (Thermo Fisher Scientific; N8010560). Fast cycling qPCR was performed with an initial activation step at 95° C. for 20 s, followed by 40 cycles of 95° C. for 1 s and 60° C. for 20 s. RPLP0 was used as the endogenous control (Thermo Fisher Scientific; 4326314E), and relative expression levels were calculated using the comparative Ct (ΔΔCt) method.

Figure 9A:
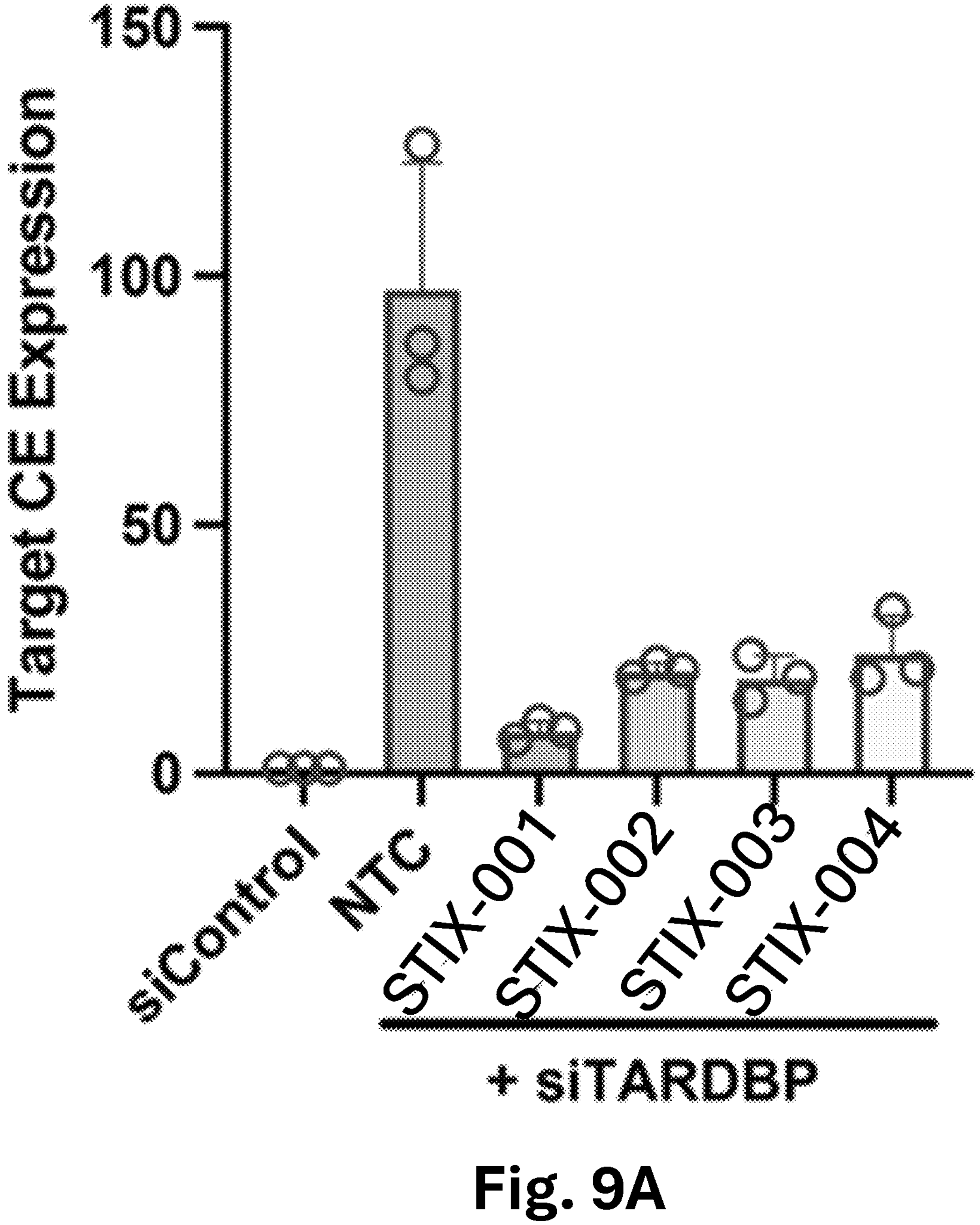
FIGS. 9A-9B show target CE expression (FIG. 9A) and tSTMN2 expression (FIG. 9B) in SH-SY5Y control cells (siControl), in cells after treatment with siRNA targeting TDP-43 (NTC), and after treatment with siTARDBP in combination with STIX-001, STIX-002, STIX-003, or STIX-004.
Figure 9B:
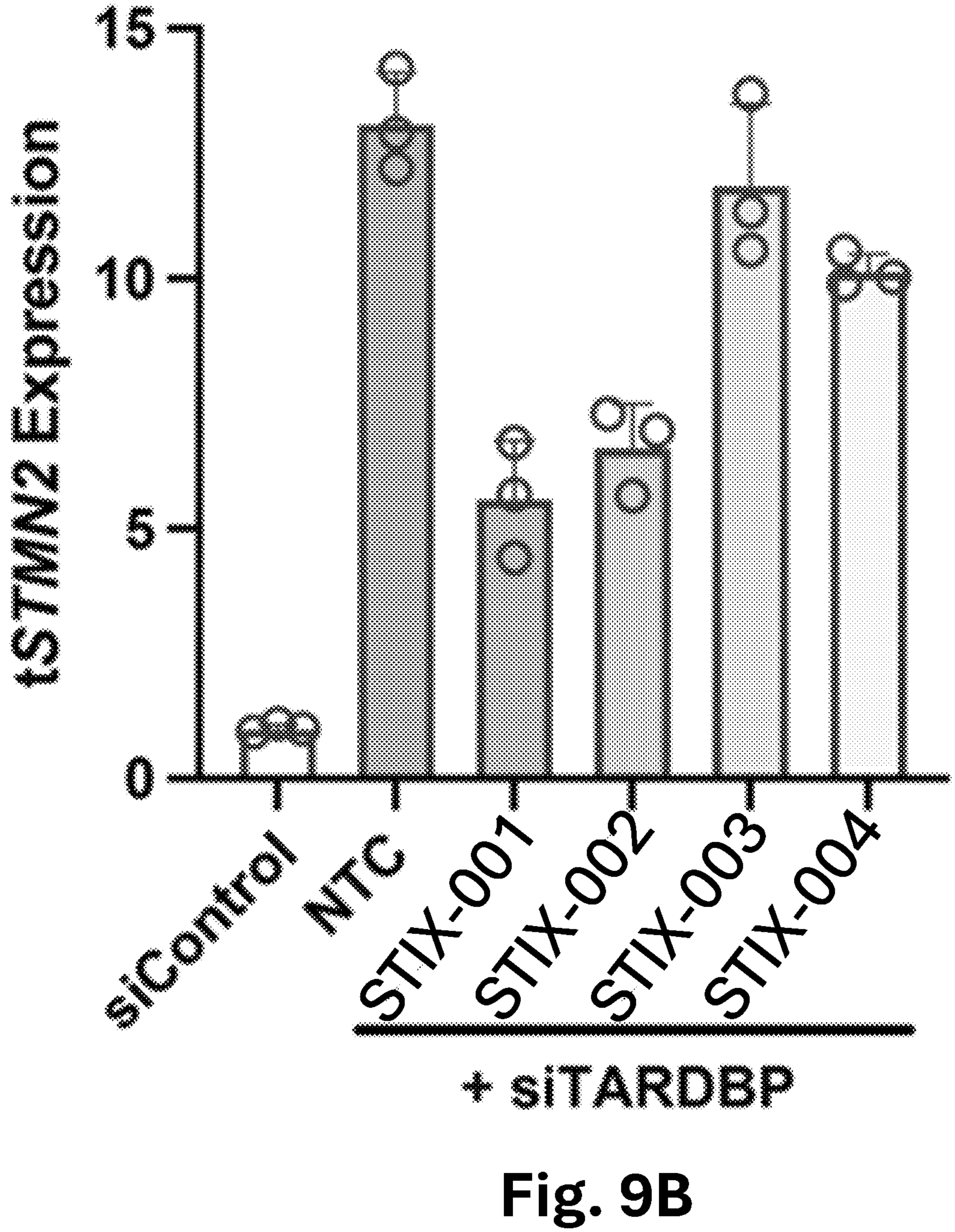

FIGS. 9A and 9B show that the observations made in SH-SY5Y cells are consistent with the data shown in Example 8 using iNeurons. Specifically, increase of CE inclusion is found in ELAVL3 and increased expression levels of truncated STMN2 (as a result of CE inclusion in the STMN2 transcript) is found in cells with TDP-43 knockdown compared to wild-type SH-SY5Y cells ("NTC"). Treatment of mutant cells with STIX-001, STIX-002, STIX-003, and STIX-004 significantly reduces the level of CE inclusion in ELAVL3. Expression levels of truncated STMN2 are partially corrected by STIX-001 and STIX-002 but not by STIX-003 and STIX-004.

Example 10: STIX-001 ASO Treatment Restores Normal Splicing in SH-SY5Y Cells with Endogenous TDP-43 Mis-Localization Wildtype SH-SY5Y cells or isogenic SH-SY5Y cells harboring an N352S mutation that results in TDP-43 loss of function and inclusion of CEs were maintained in growth medium (SH-SY5Y medium) consisting of DMEM/F12 supplemented with 10% fetal bovine serum (FBS), 100 U/mL penicillin, and 100 μg/mL streptomycin at 37° C. in a humidified incubator with 5% $CO_2$. For ASO transfection experiments, cells were seeded in 12-well tissue culture-treated plates at a density of approximately $2.5\times10^5$ cells per well, ~24 hours prior to transfection, to achieve 50-70% confluency at the time of ASO delivery. For ASO transfection, the appropriate amount of ASO was diluted in 100 μL of Opti-MEM Reduced Serum Medium to achieve a final concentration of either 20 nM or 100 nM each in a 12-well plate (1 mL total volume). Lipofectamine reagent (4 μL per well) was diluted separately in 100 μL of Opti-MEM and combined with the diluted ASO (200 μL total volume), followed by incubation at room temperature for 15-20 minutes to allow complex formation. Two hundred microliters of the ASO-lipid complexes were added dropwise to each well containing 1 mL of antibiotic-free medium. ASOs were diluted in nuclease-free water to a stock concentration of 100 μM and stored at −20° C.

At 72 hours post-transfection, cells were rinsed once with 1×PBS and total RNA was isolated using a column-based RNA extraction kit with on-column DNase digestion (Zymo). One microgram of RNA was reverse transcribed into cDNA using the High-Capacity cDNA Reverse Transcription Kit (Thermo Fisher Scientific), and the resulting cDNA was diluted with 60 μL of nuclease-free water. Quantitative PCR was performed using custom TaqMan assays targeting the ELAVL3 CE (Thermo Fisher Scientific; Assay ID AP7DWP9) and tSTMN2 CE (Thermo Fisher Scientific; Assay ID APZTKFJ), following the manufacturer's protocol. Reactions (20 μL) contained 2 μL diluted cDNA, 1 μL each of 20× target and endogenous control probes, 10 μL of 2×TaqMan Fast Advanced Master Mix, and nuclease-free water, and were run in duplicate in MicroAmp 96-well optical plates (Thermo Fisher Scientific; N8010560). Fast cycling qPCR was performed with an initial activation step at 95° C. for 20 s, followed by 40 cycles of 95° C. for 1 s and 60° C. for 20 s. RPLP0 was used as the endogenous control (Thermo Fisher Scientific; 4326314E), and relative expression levels were calculated using the comparative Ct (ΔΔCt) method.

Figure 10A:
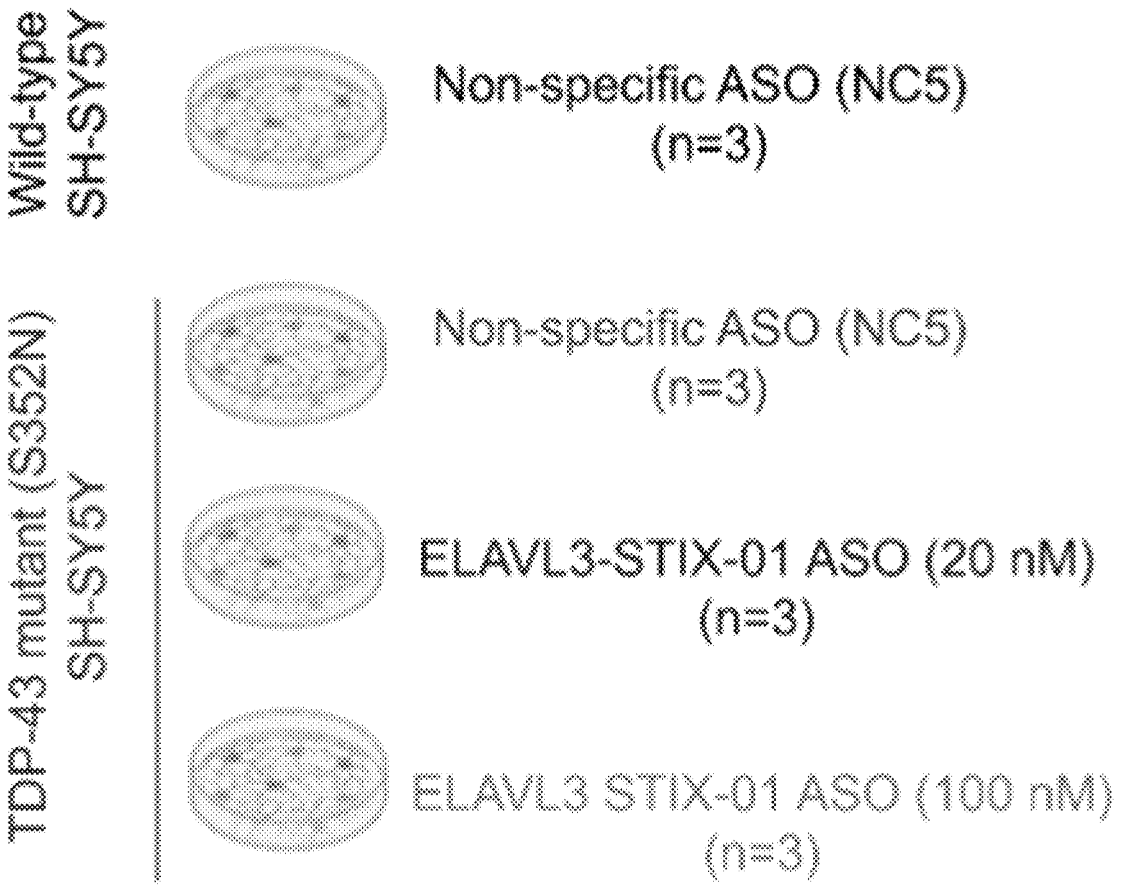
FIG. 10A shows a schematic overview of an experiment to test ASO impact on CE inclusion in ELAVL3 and STMN2 transcripts in a cell model.
Figure 10B:
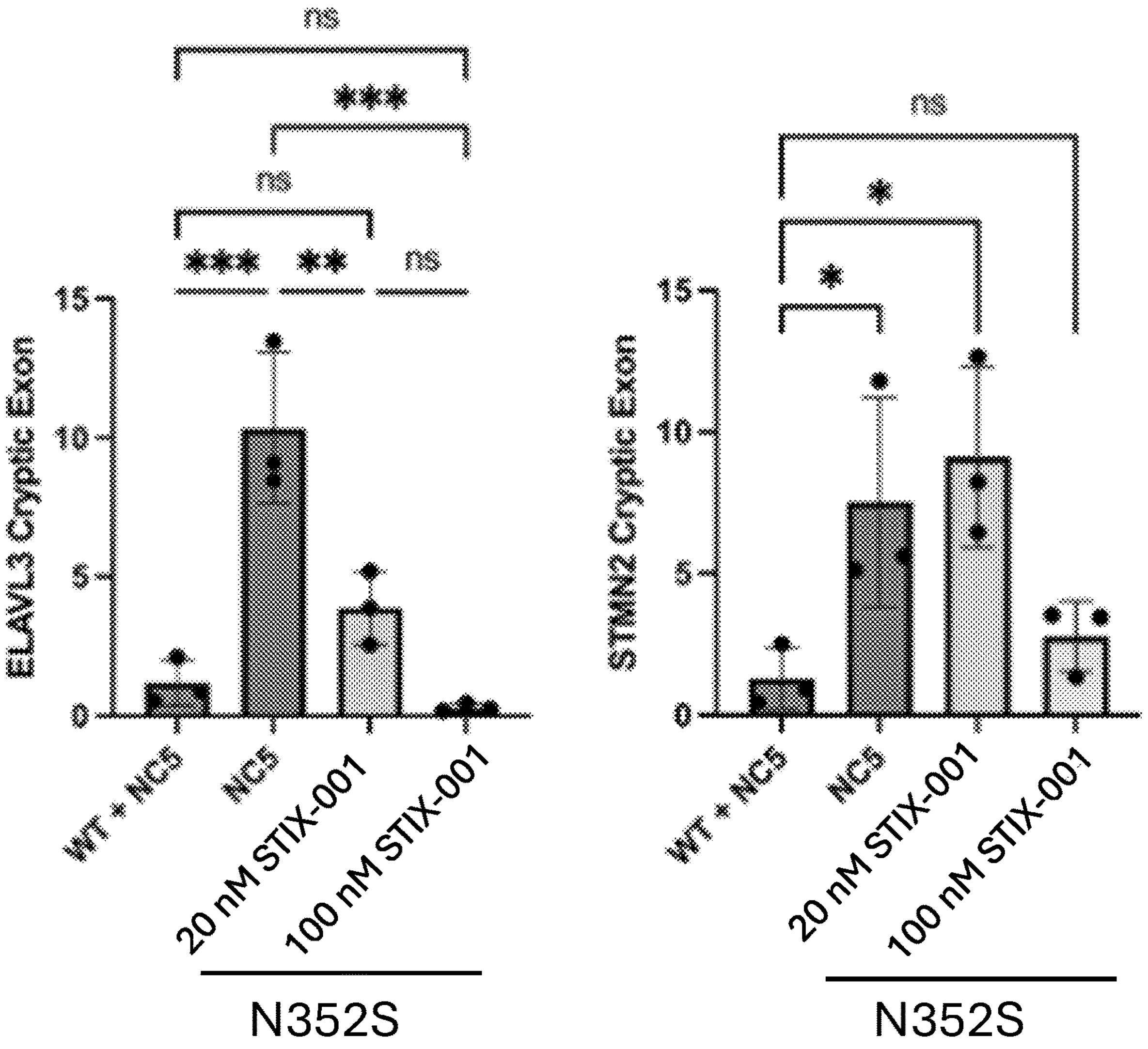
FIG. 10B shows the impact of STIX-001 at 20 nM and 100 nM on CE inclusion in ELAVL3 and STMN2 transcripts.

As shown in FIG. 10B, treatment with STIX-001 at 20 nM and 100 nM significantly reduced both ELAVL3-CE and STMN2-CE transcript levels in a dose-dependent manner, achieving near-complete suppression at 100 nM. Non-targeting control ASOs (NCS) had no effect. These findings confirm that STIX-001 effectively mitigates cryptic splicing induced by pathogenic TDP-43 mutation, restoring normal transcript architecture in a model that recapitulates disease-associated TDP-43 dysfunction.

Example 11: Treatment of Cells with STIX-001, STIX-002, or STIX-003 can Correct the Aberrant Splicing of ELAVL3 Induced by Loss of TDP-43 Function SH-SY5Y cells were maintained in growth medium (SH-SY5Y medium) consisting of DMEM/F12 supplemented with 10% fetal bovine serum (FBS), 100 U/mL penicillin, and 100 μg/mL streptomycin at 37° C. in a humidified incubator with 5% $CO_2$. For ASO transfection experiments, cells were seeded in 12-well tissue culture-treated plates at a density of approximately $2.5\times10^5$ cells per well, ~24 hours prior to transfection, to achieve 50-70% confluency at the time of ASO delivery.

For ASO/siRNA co-transfection, the appropriate amounts of ASO (non-targeting NC5 or ASO1-5) and siRNA (non-targeting control or TARDBP) were diluted together in 100 μL of Opti-MEM Reduced Serum Medium to achieve final concentrations of 100 nM each in a 12-well plate (1 mL total volume). Lipofectamine reagent (4 μL per well) was diluted separately in 100 μL of Opti-MEM and combined with the diluted ASO/siRNA mixture (200 μL total volume), followed by incubation at room temperature for 15-20 minutes to allow complex formation. 200 μL of the ASO/siRNA-lipid complexes were added dropwise to each well containing 1 mL of antibiotic-free medium.

At 72 hours post-transfection, cells were rinsed once with 1×PBS, and total RNA was isolated using a column-based RNA extraction kit with on-column DNase digestion (Zymo). One microgram of RNA was reverse transcribed into cDNA using the High-Capacity cDNA Reverse Transcription Kit (Thermo Fisher Scientific), and the resulting cDNA was diluted with 60 μL of nuclease-free water. Quantitative PCR was performed using a custom TaqMan assay targeting the ELAVL3 CE (ThermoFisher Scientific; Assay ID AP7DWP9) (ThermoFisher Scientific; Assay ID APZTKFJ) or a commercial Taqman probeset measuring ELAVL3 (Hs00154959_ml) following the manufacturer's protocol. Reactions (20 μL) contained 2 μL diluted cDNA, 1 μL each of 20× target and endogenous control probes, 10 μL of 2×TaqMan Fast Advanced Master Mix, and nuclease-free water, and were run in duplicate in MicroAmp 96-well optical plates (Thermo Fisher Scientific; N8010560). Fast cycling qPCR was performed with an initial activation step at 95° C. for 20 s, followed by 40 cycles of 95° C. for 1 s and 60° C. for 20 s. RPLP0 was used as the endogenous control (Thermo Fisher Scientific; 4326314E), and relative expression levels were calculated using the comparative Ct (ΔΔCt) method.

Figure 11A:
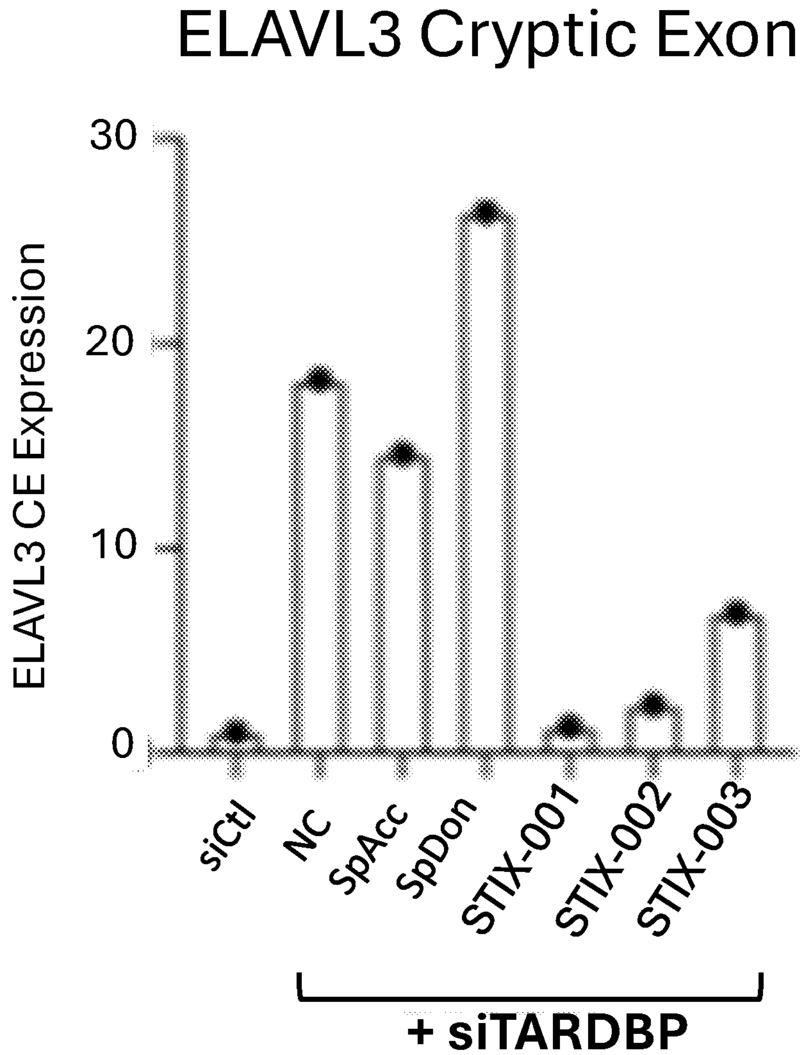
FIGS. 11A-11B show the impact of treatment with one of: siCtl (siControl), a non-targeting ASO (NC), SpAcc, SpDon, STIX-001, STIX-002, or STIX-003, respectively, on ELAVL3 CE expression (FIG. 11A), or expression of the region between ELAVL3 Exon 3 and Exon 4 ("Ex3-Ex4") (FIG. 11B).
Figure 11B:
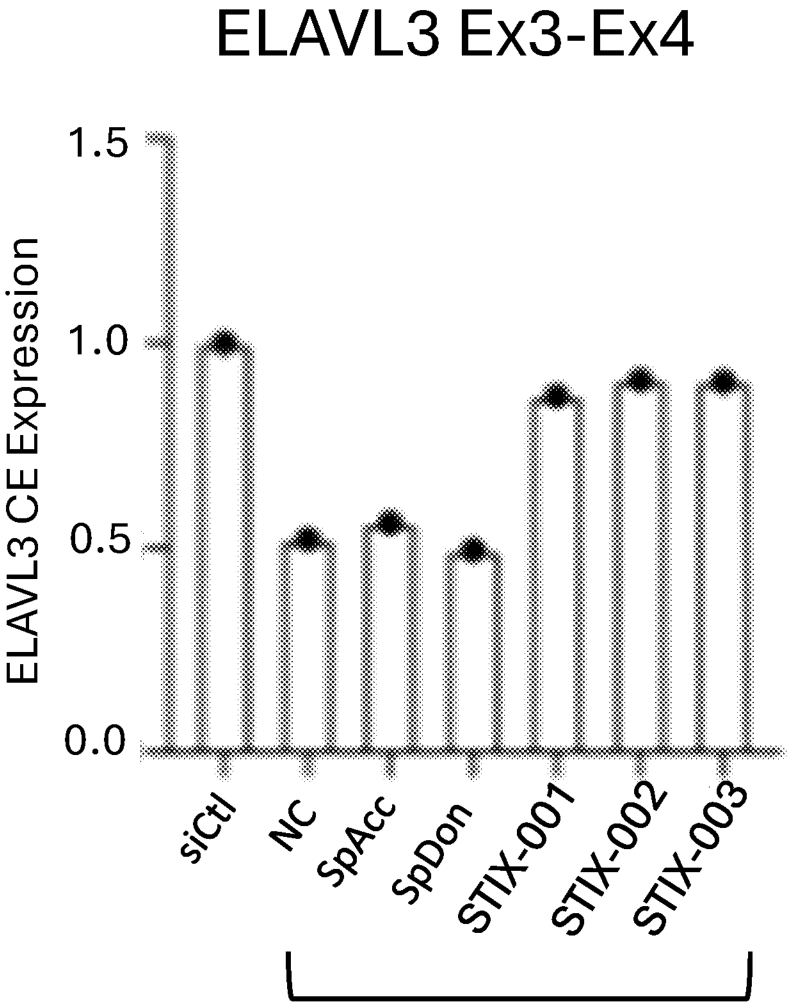

FIGS. 11A and 11B demonstrate that treatment of cells with STIX-001, STIX-002, or STIX-003 can correct the aberrant splicing of ELAVL3 induced by loss of TDP-43 function. TDP-43 is a splicing factor, and loss of TDP-43 function or expression leads to aberrant splicing events in many transcripts, including ELAVL3. The data presented here shows that ASOs can correct these aberrant splicing events.

Example 12: Treatment Impact on CE Inclusion

SH-SY5Y cells were maintained in growth medium (SH-SY5Y medium) consisting of DMEM/F12 supplemented with 10% fetal bovine serum (FBS), 100 U/mL penicillin, and 100 μg/mL streptomycin at 37° C. in a humidified incubator with 5% $CO_2$. For ASO transfection experiments, cells were seeded in 12-well tissue culture-treated plates at a density of approximately $2.5\times10^5$ cells per well, ~24 hours prior to transfection, to achieve 50-70% confluency at the time of ASO delivery.

For ASO/siRNA co-transfection, the appropriate amounts of ASO (non-targeting NC5, SpAcc, SpDon, STIX-001-STIX-004) and siRNA (non-targeting control, TARDBP, ELAVL3) were diluted together in 100 μL of Opti-MEM Reduced Serum Medium to achieve final concentrations of 100 nM each in a 12-well plate (1 mL total volume). Lipofectamine reagent (4 μL per well) was diluted separately in 100 μL of Opti-MEM and combined with the diluted ASO/siRNA mixture (200 μL total volume), followed by incubation at room temperature for 15-20 minutes to allow complex formation. 200 μL of the ASO/siRNA-lipid complexes were added dropwise to each well containing 1 mL of antibiotic-free medium.

At 72 hours post-transfection, cells were rinsed once with 1×PBS, and total RNA was isolated using a column-based RNA extraction kit with on-column DNase digestion (Zymo). One microgram of RNA was reverse transcribed into cDNA using the High-Capacity cDNA Reverse Transcription Kit (ThermoFisher Scientific), and the resulting cDNA was diluted with 60 μL of nuclease-free water. Quantitative PCR was performed using a custom TaqMan assays targeting the ELAVL3 CE (ThermoFisher Scientific; Assay ID AP7DWP9) (ThermoFisher Scientific; Assay ID APZTKFJ) and tSTMN2 CE (Thermo Fisher Scientific; Assay ID APZTKFJ) following the manufacturer's protocol. Reactions (20 μL) contained 2 μL diluted cDNA, 1 μL each of 20× target and endogenous control probes, 10 μL of 2×TaqMan Fast Advanced Master Mix, and nuclease-free water, and were run in duplicate in MicroAmp 96-well optical plates (ThermoFisher Scientific; N8010560). Fast cycling qPCR was performed with an initial activation step at 95° C. for 20 s, followed by 40 cycles of 95° C. for 1 s and 60° C. for 20 s. RPLP0 was used as the endogenous control (ThermoFisher Scientific; 4326314E), and relative expression levels were calculated using the comparative Ct (ΔΔCt) method.

Figure 12A:
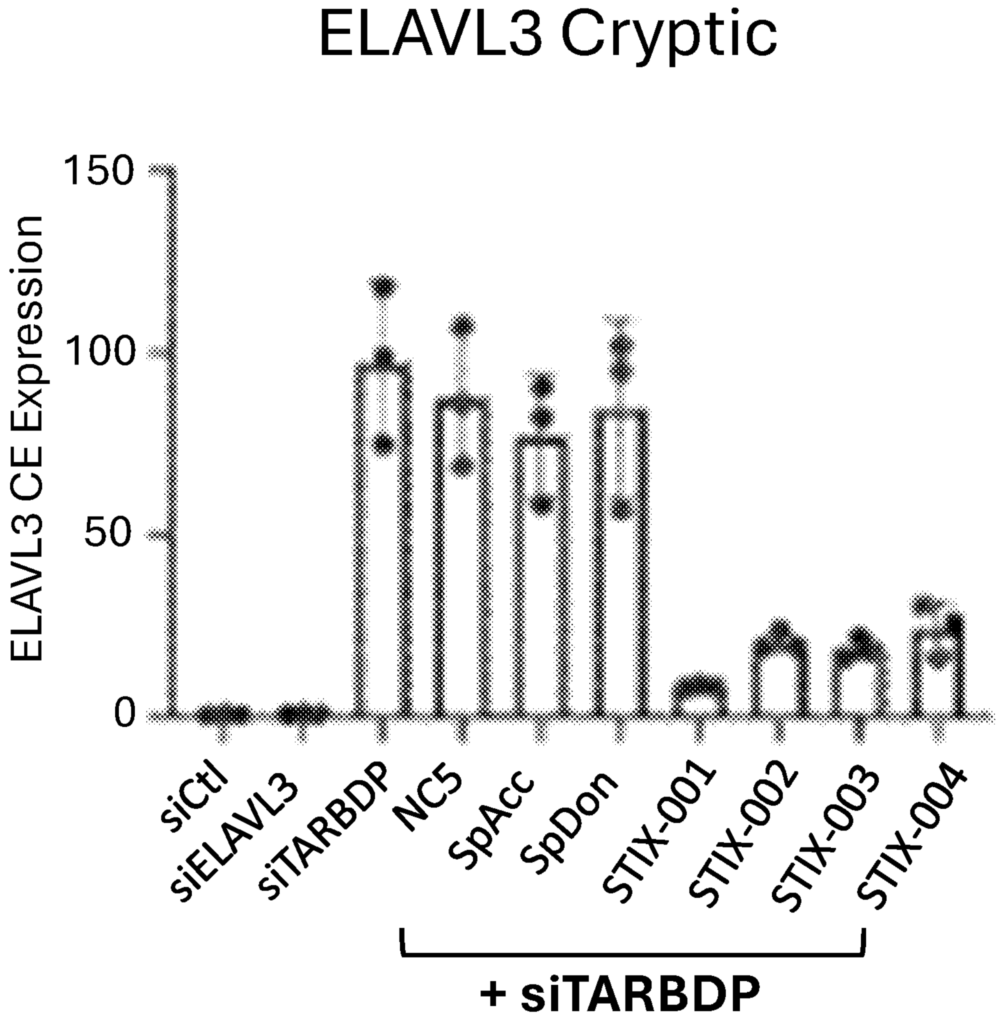
FIGS. 12A-12B show the impact of treatment with one of: siCtl (siControl), a non-targeting ASO (NC), SpAcc, SpDon, STIX-001, STIX-002, or STIX-003, respectively, on CE inclusion in the ELAVL3 transcript (FIG. 12A) and the STMN2 transcript (FIG. 12B), respectively.
Figure 12B:
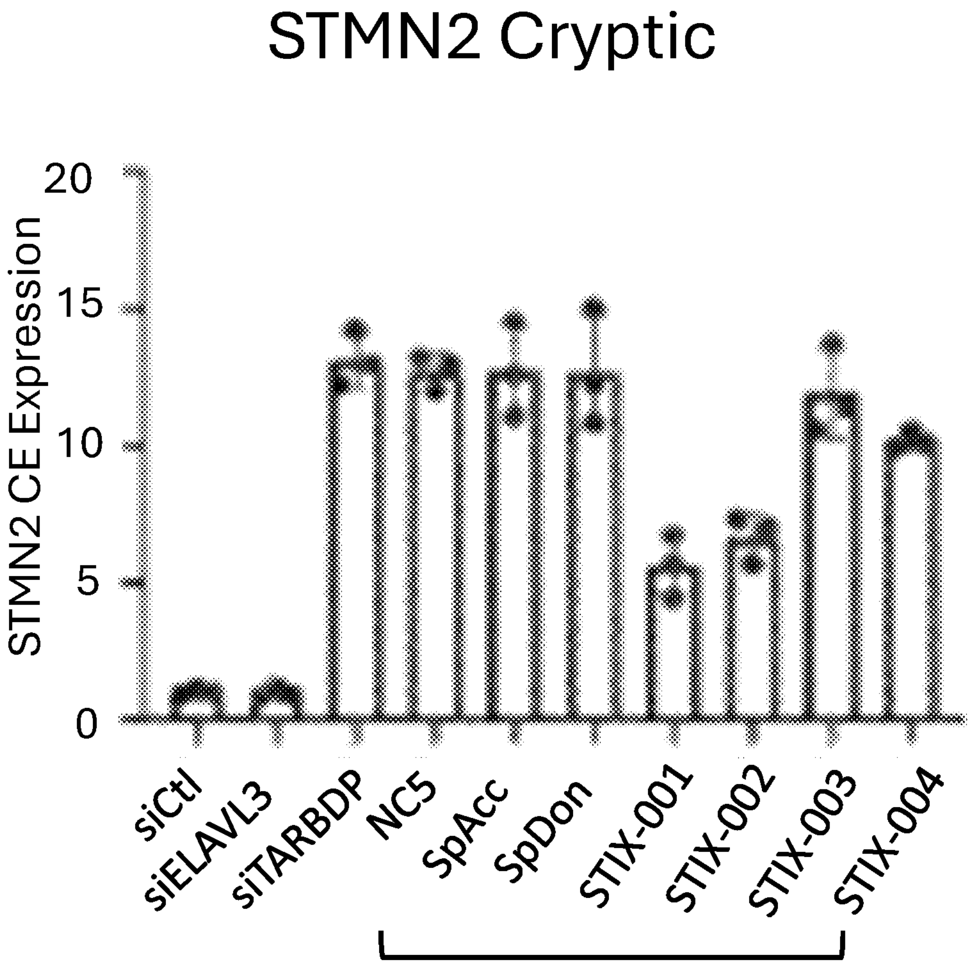

FIGS. 12A and 12B show the impact of ASOs on aberrant splicing in the STMN2 transcript. Treatment with ASOs results in only partial CE correction and is limited to STIX-001 and STIX-002. This is in contrast to the impact on CE inclusion in the ELAVL3 transcript, where ASOs show a complete reversal of the defect induced by TDP-43. Surprisingly, while STIX-003 and STIX-004 show significant impact on the inclusion of CEs in ELAVL3 transcripts which are comparable to the effect of STIX-001 and STIX-002, the effect of CE inclusion in the STMN2 transcript is different between STIX-001 and STIX-002 on one side and STIX-003 and STIX-004 on the other, with the first group showing an impact on STMN2 splicing events while the second group of ASOs does not.

Example 13: Restoration of ELAVL3 Expression Corrects Several TDP-43-Regulated Cryptic Exon Events SmartPool siRNAs targeting either a non-targeting scrambled control or TARDBP (Dharmacon) were transfected at a final concentration of 100 nM, together with either a non-targeting control ASO (NC5), or STIX-001 at a final concentration of 100 nM, using Lipofectamine RNAiMAX according to the manufacturer's instructions. At 24 and 72 hours post-transfection, the culture medium was replaced with fresh SH-SY5Y medium. At 72 hours post-transfection, cells were rinsed once with 1×PBS and lysed in TRIzol reagent. Following chloroform phase separation, the aqueous phase was collected, diluted 1:1 with ethanol, and purified using a column-based RNA cleanup protocol with on-column DNase digestion (Zymo). 700 nanograms of RNA were reverse transcribed into cDNA using the High-Capacity cDNA Reverse Transcription Kit (ThermoFisher Scientific), and the resulting cDNA was diluted with 60 μL of nuclease-free water. Quantitative PCR was performed using TaqMan Custom Gene Expression Assays for ELAVL3 CE (ThermoFisher Scientific; Assay ID AP7DWP9), tSTMN2 (ThermoFisher Scientific; Assay ID APZTKFJ), PTPRN2 CE (ThermoFisher Scientific), GRAMD1A CE (ThermoFisher Scientific), GPX7 CE (ThermoFisher Scientific), and CAMK2B CE (ThermoFisher Scientific; Assay ID APCFA9U) following the manufacturer's protocol. Reactions (20 µL) contained 2 µL diluted cDNA, 1 µL each of 20× target and endogenous control probes, 10 µL of 2×TaqMan Fast Advanced Master Mix, and nuclease-free water, and were run in duplicate in MicroAmp 96-well optical plates (ThermoFisher Scientific; N8010560). Fast cycling qPCR was performed with an initial activation step at 95° C. for 20 s, followed by 40 cycles of 95° C. for 1 s and 60° C. for 20 s. RPLP0 was used as the endogenous control (ThermoFisher Scientific; 4326314E), and relative expression levels were calculated using the comparative Ct (ΔΔCt) method.

Figure 13:
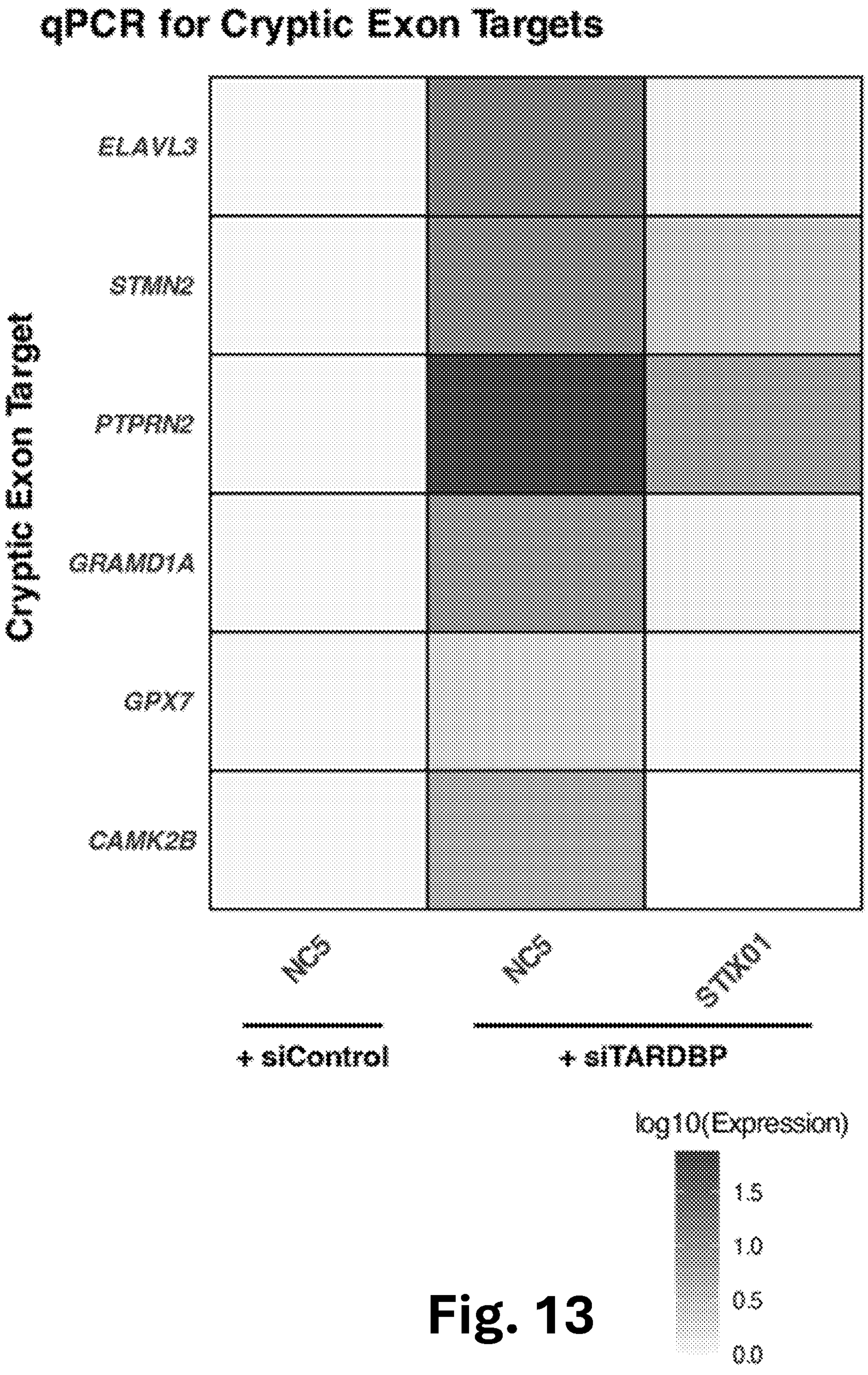
FIG. 13 is a heatmap showing expression values for multiple TDP-43 regulated CE splicing events in cells treated with a non-targeting siRNA (siControl) and non-targeting ASO (NC5), TARDBP siRNA (siTARDBP) with NC5, or TARDBP siRNA (siTARDBP) with the ELAVL3 cryptic exon targeting ASO STIX-001.

FIG. 13 is a heatmap showing log 10-transformed qPCR expression values for multiple TDP-43 regulated cryptic exon splicing events in SH-SY5Y cells treated with a non-targeting siRNA (siControl) and non-targeting ASO (NC5), TARDBP siRNA (siTARDBP) with NC5, or TARDBP siRNA (siTARDBP) with the ELAVL3 cryptic exon targeting ASO STIX-001. As shown in FIG. 13, restoration of ELAVL3 expression corrects several TDP-43-regulated cryptic exon events.

SH-SY5Y cells were cultured in DMEM supplemented with 10% FBS and penicillin/streptomycin and seeded in 150-mm dishes at $2.5\times10^6$ cells per dish. Cells were grown for 72-96 h to ~80-90% confluence, washed with cold PBS, scraped, and pelleted by centrifugation.

Cell pellets were lysed in NP-40 lysis buffer (100 mM KCl, 25 mM EDTA, 5 mM $MgCl_2$, 10 mM HEPES pH 7.0, 0.5% NP-40, 10% glycerol) supplemented with DTT, protease inhibitors, RNase inhibitor, and vanadyl ribonucleoside complexes. Lysates were incubated on ice for 30 min, briefly sonicated, and clarified by centrifugation at 4° C. for 15 min. Protein concentration was measured by BCA assay.

For each immunoprecipitation, equal amounts of lysate (12 mg total protein) were diluted in NT2 buffer supplemented with EDTA, DTT, and RNase inhibitors and precleared with magnetic Protein A Dynabeads for 30 min at 4° C. Antibodies (10 µg; ELAVL3, TDP-43, or control IgG) were incubated with Protein A Dynabeads in NT2 buffer containing 5% BSA overnight at 4° C. with rotation. Antibody-coupled beads were washed and incubated with precleared lysate for 3-5 h at room temperature with rotation. Beads were washed five times with NT2 buffer containing 150 mM NaCl.

RNA-protein complexes were digested with proteinase K in SDS-containing buffer at 55° C., and RNA was extracted using acid phenol-chloroform followed by chloroform extraction. RNA was precipitated with isopropanol in the presence of sodium acetate, $MgCl_2$, and linear acrylamide, washed with ethanol, air-dried, and resuspended in nuclease-free water. Input and immunoprecipitated samples were retained for downstream analysis by western blot and RT-qPCR.

Equal volumes of RNA were reverse transcribed into cDNA using the High-Capacity cDNA Reverse Transcription Kit (ThermoFisher Scientific). Quantitative PCR was performed using TaqMan Gene Expression Assays for TARDBP or GAPDH or custom Taqman assays for ELAVL3 CE following the manufacturer's protocol. Reactions (20 µL) contained cDNA, 1 µL each of 20× target Taqman probes, 10 µL of 2×TaqMan Fast Advanced Master Mix, and nuclease-free water, and were run in duplicate in MicroAmp 96-well optical plates (ThermoFisher Scientific; N8010560). Fast cycling qPCR was performed with an initial activation step at 95° C. for 20 s, followed by 40 cycles of 95° C. for 1 s and 60° C. for 20 s. Relative enrichment was calculated using a comparative Ct (ΔCt) method between ELAVL3 or TDP-43 immunoprecipitation compared to IgG immunoprecipitation.

Figure 14A:
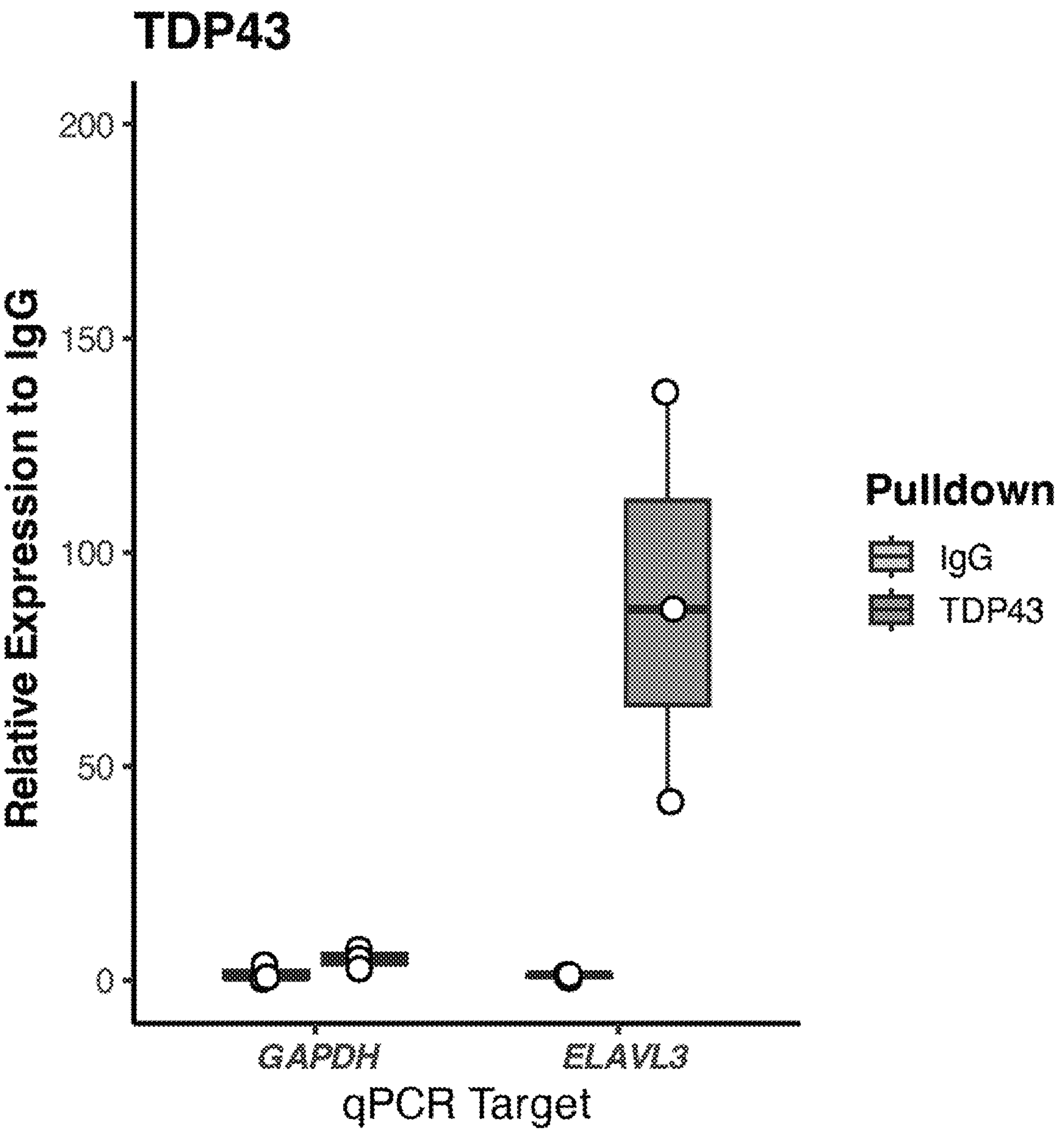
FIG. 14A shows relative expression of ELAVL3 transcripts in TDP-43 immunoprecipitates compared to IgG controls.
Figure 14B:
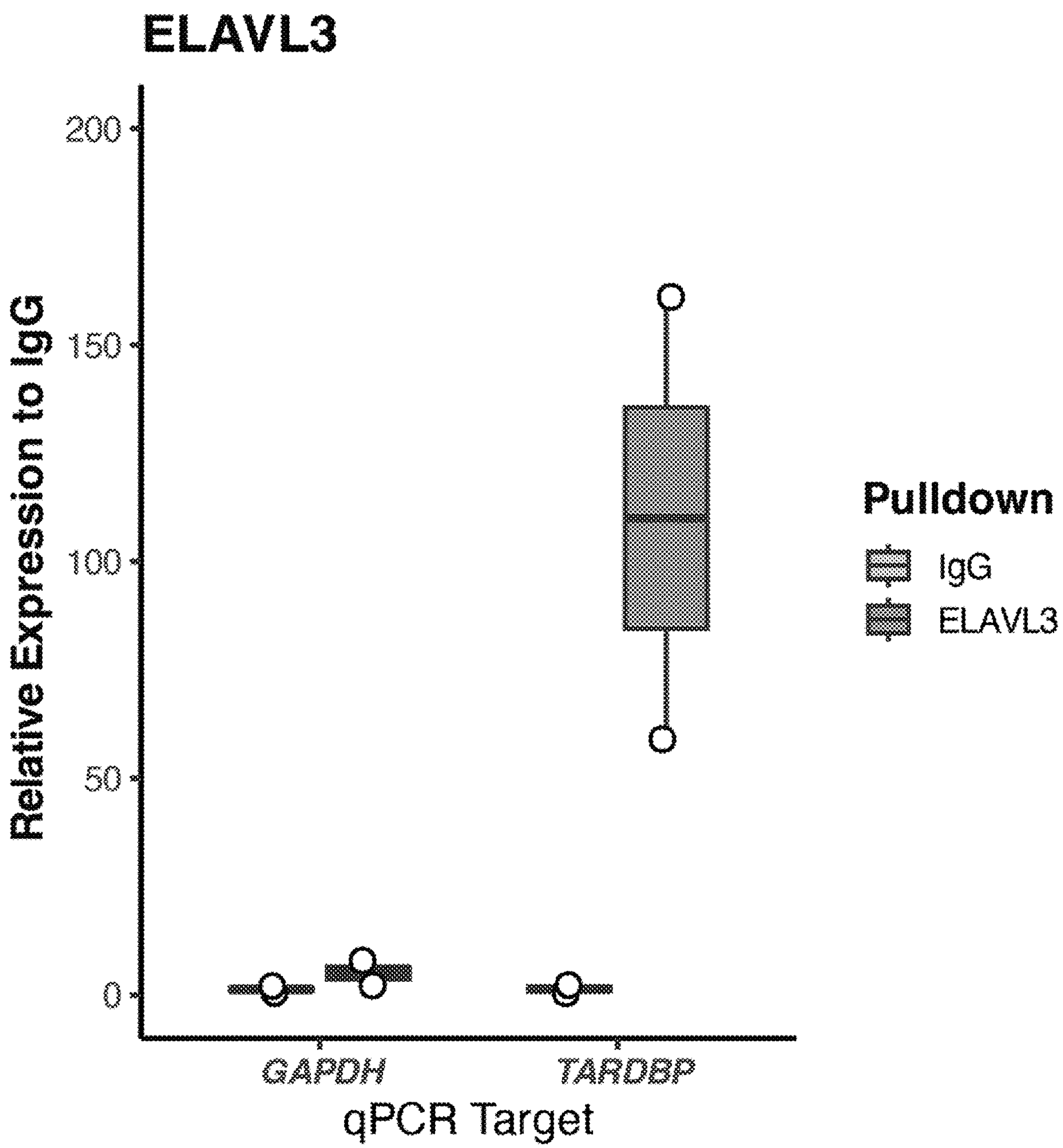
FIG. 14B shows relative expression of TARDBP transcripts in ELAVL3 immunoprecipitates compared to IgG controls.

As shown in FIG. 14A, RNA immunoprecipitation of TDP-43 in SH-SY5Y cells followed by qPCR demonstrates robust enrichment of ELAVL3 transcripts in TDP-43 immunoprecipitates relative to IgG controls, while GAPDH shows minimal enrichment. FIG. 14B shows that RNA immunoprecipitation of ELAVL3 in SH-SY5Y cells followed by qPCR results in robust enrichment of TARDBP transcripts in ELAVL3 immunoprecipitates relative to IgG controls, while GAPDH shows minimal enrichment.

Figure 15A:
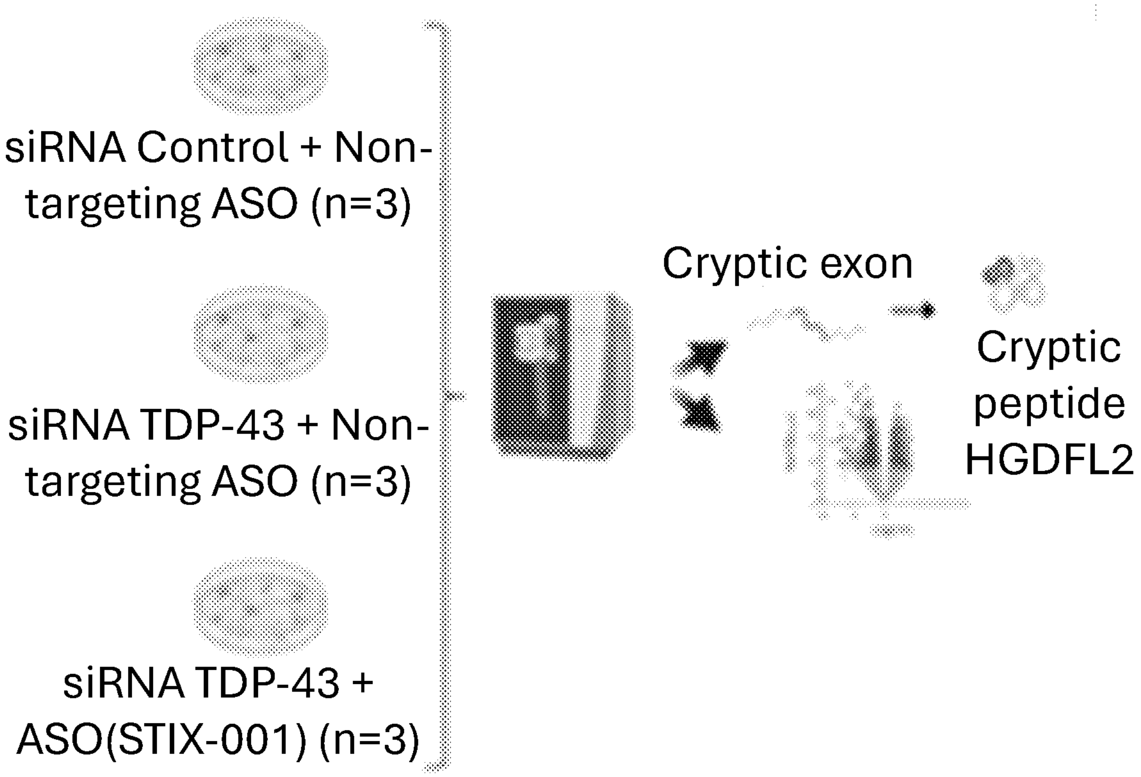
FIG. 15A shows an experimental set-up and a schematic analysis flow for SH-SY5Y cells treated with an agent targeting TDP-43.

Example 15: Proteomic Profiling of ELAVL3 ASO Treatment in TDP-43-Depleted Cells To evaluate global effects of ELAVL3 splice correction, quantitative data-independent acquisition (DIA) proteomics were performed on human SH-SY5Y neuroblastoma cells following siRNA-mediated TDP-43 knockdown (siTDP-43) and ASO treatment. This schematic is shown in FIG. 15A.

Figure 15B:
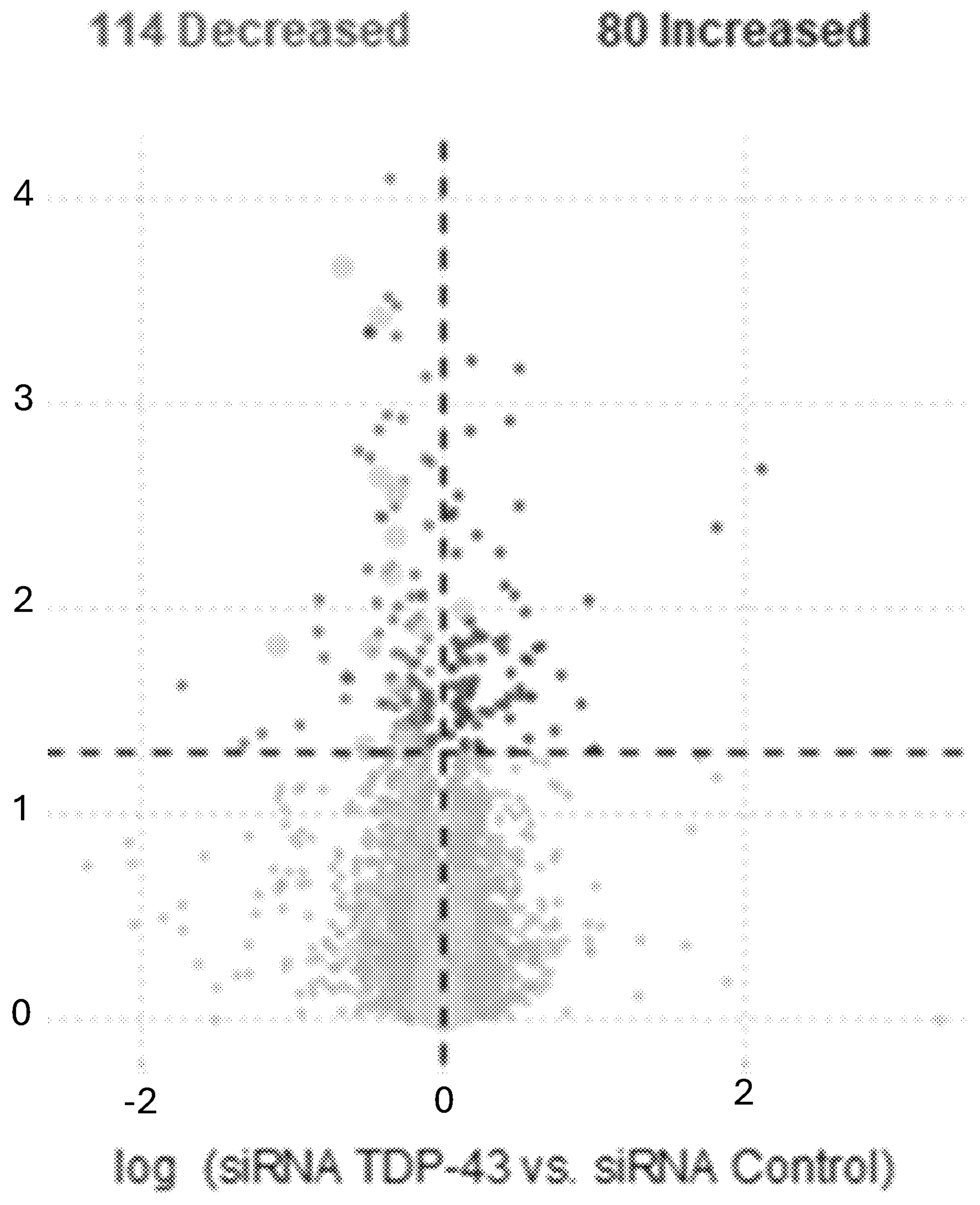
FIG. 15B shows the proteomic fingerprint of SH-SY5Y cells under conditions of reduced TDP-43 expression compared to cells treated with a control siRNA.

FIG. 15B shows the proteomic fingerprint of SH-SY5Y cells under conditions of reduced TDP-43 expression compared to cells treated with a control siRNA. Expression levels of 114 proteins are reduced, while expression levels of 80 proteins are increased. FIG. 15B does not contain any data from ASO-treated cells. Most transcripts that include CE show reduced protein expression (top left quadrant of the plot).

Example 16: Rescue of TDP-43 Target Proteins Harboring CEs

Figure 16:
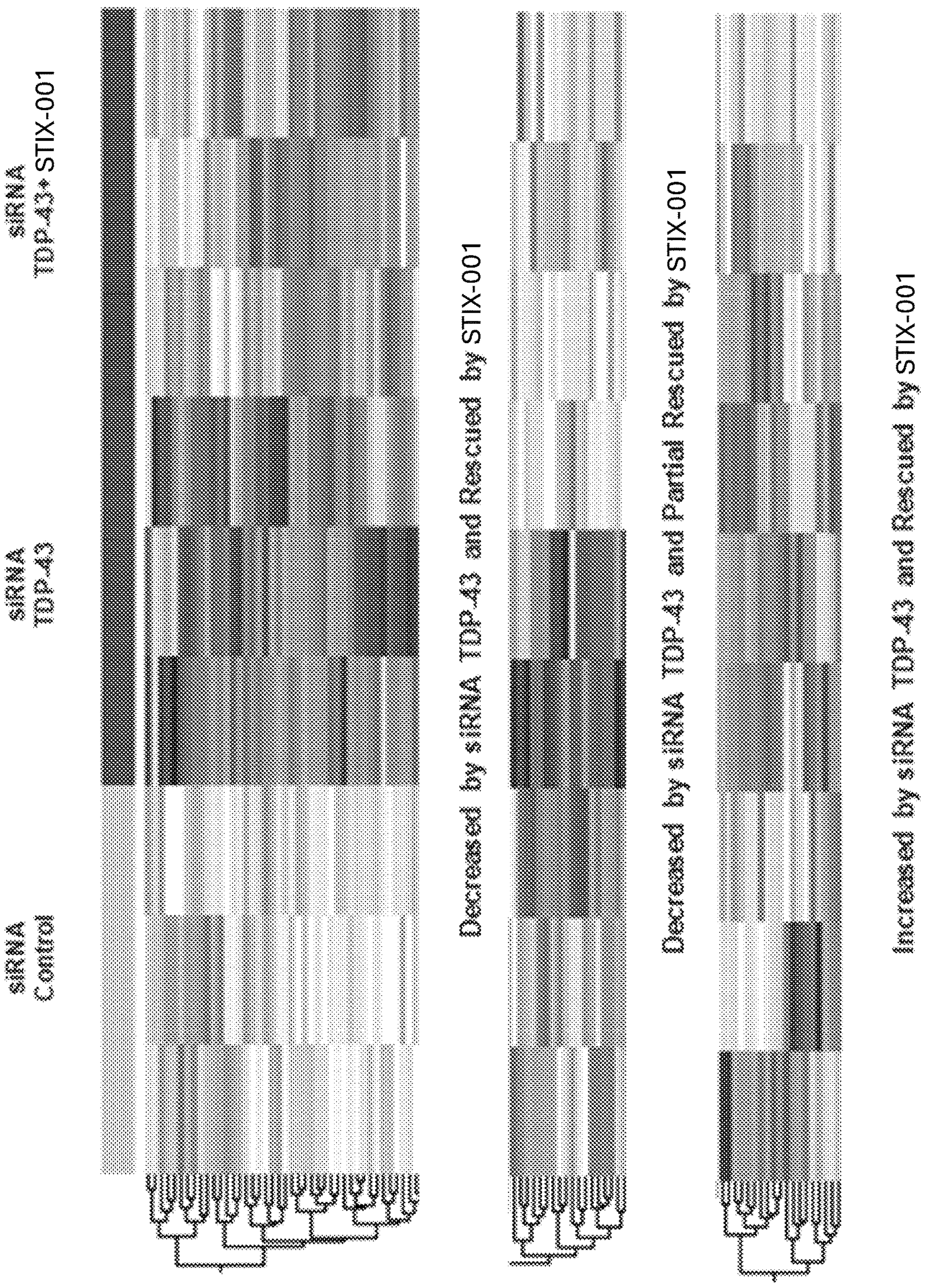
FIG. 16 shows the proteome-wide impact of treating SH-SY5Y cells with either siRNA control, siRNA TDP-43, or siRNA TDP-43 and STIX-001.
Figure 17:
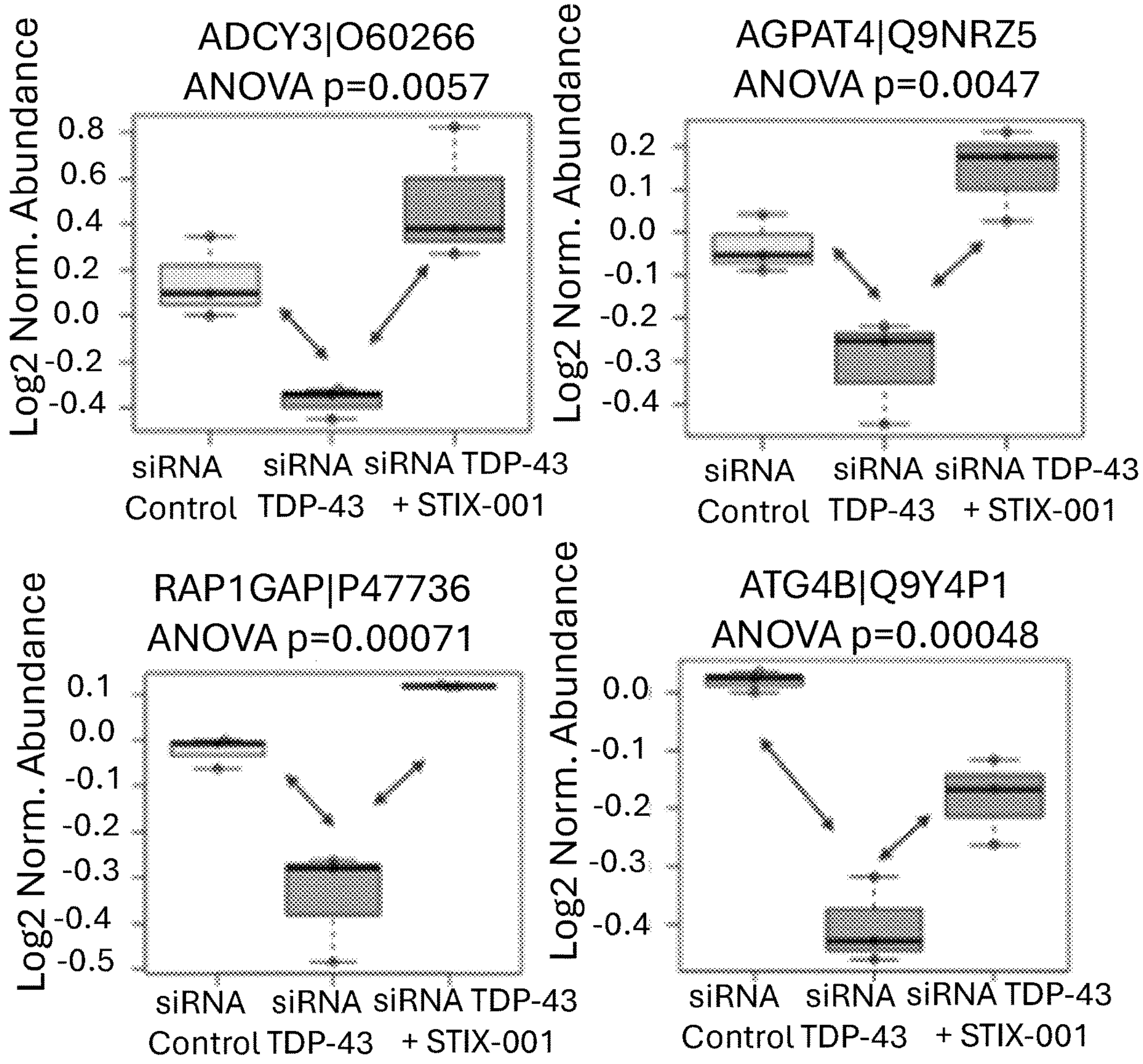
FIG. 17 shows levels of a subset of proteins that are specifically relevant to neuronal function in ALS after cellular treatment with siRNA control, siRNA TDP-43, or siRNA TDP-43 and STIX-001.
Figure 17:
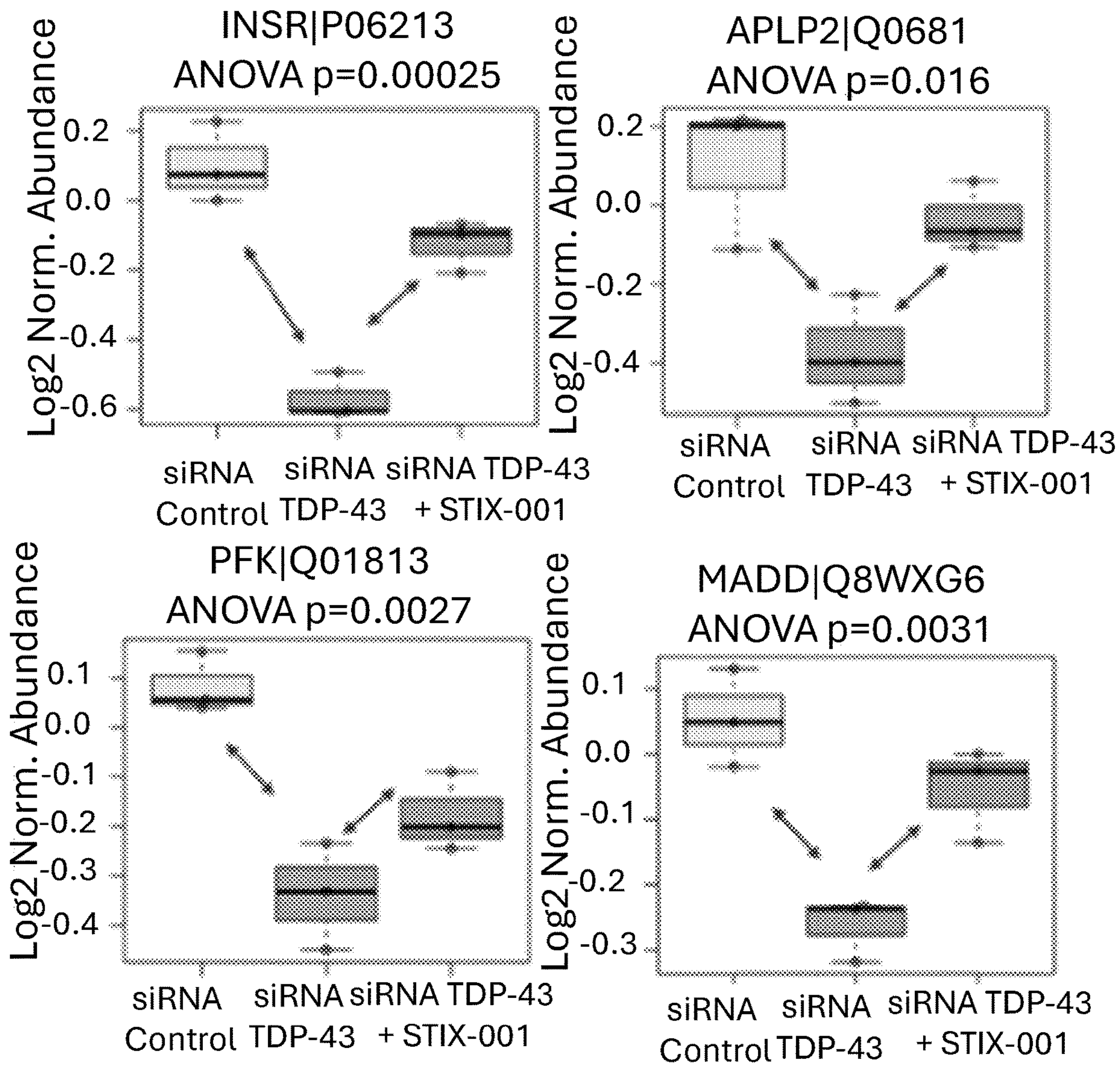

SH-SY5Y cells were treated with a siRNA targeting TDP-43 (to reduce TDP-43 expression levels) and with either a control ASO or STIX-001. FIG. 16 shows the proteome-wide impact of treating SH-SY5Y cells with TDP-43 siRNA alone and in combination with STIX-001. 194 proteins were found to significantly differ between cells treated with a control siRNA and cells treated with TDP-43 siRNA. Compared to cells treated with a control siRNA (left column), cells treated with TDP-43 siRNA result in a significant number of proteins with reduced expression levels (middle column in top and middle panel). Conversely, treatment with TDP-43 and STIX-001 fully or partially restores ~66% (n=128) of the differentially abundant proteins due to TDP-43 knockdown back to control levels. Within this restored group, ~35% of proteins (n=68) were fully restored (right column, top and bottom panels) and ~30% (n=60) partially restored (right column, middle panel), following treatment with STIX-001.

Example 17: Correction of CE Inclusion in TDP-43 (S352N) Mutant Cells

To assess therapeutic potential in a disease-relevant genetic context, STIX-001 was evaluated in a TDP-43 (S352N) mutant SH-SY5Y cell line, which exhibits impaired RNA-binding function and elevated cryptic splicing activity. SH-SY5Y cells were maintained in growth medium (SH-SY5Y medium) consisting of DMEM/F12 supplemented with 10% fetal bovine serum (FBS), 100 U/mL penicillin, and 100 µg/mL streptomycin at 37° C. in a humidified incubator with 5% $CO_2$. For ASO transfection experiments, cells were seeded in 12-well tissue culture-treated plates at a density of approximately $2.5\times10^5$ cells per well, ~24 hours prior to transfection, to achieve 50-70% confluency at the time of ASO delivery.

SmartPool siRNAs targeting either a non-targeting scrambled control or TARDBP (Dharmacon) were transfected at a final concentration of 100 nM, together with either a non-targeting control ASO (NC5), STIX-001, or STIX-002 at a final concentration of 100 nM, using Lipofectamine RNAiMAX according to the manufacturer's instructions. At 24 and 72 hours post-transfection, the culture medium was replaced with fresh SH-SY5Y medium. At 96 hours post-transfection, cells were rinsed once with 1×PBS and lysed in 8 M urea buffer (8 M urea, 30 mM Tris-HCl, pH 8.0, 1×HALT protease/phosphatase inhibitor cocktail). Lysates were sonicated for three cycles of 3 seconds on and 3 seconds off at 30% power. Protein concentrations were determined using a BCA assay, and lysates were normalized to a final concentration of 1.5 μg/μL in 8 M urea buffer.

Protein lysates (20 ug) were digested with trypsin and endopeptidase LysC as previously described including indexed retention time standards (iRTs) (Biognosys Inc). Each

SEQUENCE LISTING

```
Sequence total quantity: 23
SEQ ID NO: 1            moltype = DNA  length = 167
FEATURE                 Location/Qualifiers
source                  1..167
                        mol_type = other DNA
                        organism = synthetic construct
SEQUENCE: 1
gtgcatgtga cactgtgact ccggctgtga cctgatgggg cctcagggat gcgtctggct  60
ctggcaggat gtttgtgtgt caccgcgatg ttgtgtgggt gtgtctacct gtgccctgct  120
ctgagggatt gagtgtgata tcgtgtgttt gtgctgcgct gtgatgg                167

SEQ ID NO: 2            moltype = DNA  length = 20
FEATURE                 Location/Qualifiers
source                  1..20
                        mol_type = other DNA
                        organism = synthetic construct
SEQUENCE: 2
agtcacagtg tcacatgcac                                              20

SEQ ID NO: 3            moltype = DNA  length = 20
FEATURE                 Location/Qualifiers
source                  1..20
                        mol_type = other DNA
                        organism = synthetic construct
SEQUENCE: 3
gtcacatgca cctgtcaaat                                              20

SEQ ID NO: 4            moltype = DNA  length = 11
FEATURE                 Location/Qualifiers
source                  1..11
                        mol_type = other DNA
                        organism = synthetic construct
SEQUENCE: 4
gtcacatgca c                                                       11

SEQ ID NO: 5            moltype = DNA  length = 20
FEATURE                 Location/Qualifiers
source                  1..20
                        mol_type = other DNA
                        organism = synthetic construct
SEQUENCE: 5
accacatacc catcacagcg                                              20

SEQ ID NO: 6            moltype = DNA  length = 21
FEATURE                 Location/Qualifiers
source                  1..21
                        mol_type = other DNA
                        organism = synthetic construct
SEQUENCE: 6
acagccggag tcacagtgtc a                                            21

SEQ ID NO: 7            moltype = DNA  length = 23
FEATURE                 Location/Qualifiers
source                  1..23
                        mol_type = other DNA
                        organism = synthetic construct
SEQUENCE: 7
ccatcaggtc acagccggag tca                                          23

SEQ ID NO: 8            moltype = DNA  length = 20
FEATURE                 Location/Qualifiers
```

```
source                  1..20
                        mol_type = other DNA
                        organism = synthetic construct
SEQUENCE: 8
ccagacgcat ccctgaggcc                                              20

SEQ ID NO: 9            moltype = DNA  length = 20
FEATURE                 Location/Qualifiers
source                  1..20
                        mol_type = other DNA
                        organism = synthetic construct
SEQUENCE: 9
cgcggtgaca cacaaacatc                                              20

SEQ ID NO: 10           moltype = RNA  length = 167
FEATURE                 Location/Qualifiers
source                  1..167
                        mol_type = other RNA
                        organism = synthetic construct
SEQUENCE: 10
gtgcatgtga cactgtgact ccggctgtga cctgatgggg cctcagggat gcgtctggct  60
ctggcaggat gtttgtgtgt caccgcgatg ttgtgtgggt gtgtctacct gtgccctgct  120
ctgagggatt gagtgtgata tcgtgtgttt gtgctgcgct gtgatgg                167

SEQ ID NO: 11           moltype = RNA  length = 20
FEATURE                 Location/Qualifiers
source                  1..20
                        mol_type = other RNA
                        organism = synthetic construct
SEQUENCE: 11
agtcacagtg tcacatgcac                                              20

SEQ ID NO: 12           moltype = RNA  length = 20
FEATURE                 Location/Qualifiers
source                  1..20
                        mol_type = other RNA
                        organism = synthetic construct
SEQUENCE: 12
gtcacatgca cctgtcaaat                                              20

SEQ ID NO: 13           moltype = RNA  length = 11
FEATURE                 Location/Qualifiers
source                  1..11
                        mol_type = other RNA
                        organism = synthetic construct
SEQUENCE: 13
gtcacatgca c                                                       11

SEQ ID NO: 14           moltype = RNA  length = 20
FEATURE                 Location/Qualifiers
source                  1..20
                        mol_type = other RNA
                        organism = synthetic construct
SEQUENCE: 14
accacatacc catcacagcg                                              20

SEQ ID NO: 15           moltype = RNA  length = 21
FEATURE                 Location/Qualifiers
source                  1..21
                        mol_type = other RNA
                        organism = synthetic construct
SEQUENCE: 15
acagccggag tcacagtgtc a                                            21

SEQ ID NO: 16           moltype = RNA  length = 23
FEATURE                 Location/Qualifiers
source                  1..23
                        mol_type = other RNA
                        organism = synthetic construct
SEQUENCE: 16
ccatcaggtc acagccggag tca                                          23

SEQ ID NO: 17           moltype = RNA  length = 20
FEATURE                 Location/Qualifiers
source                  1..20
                        mol_type = other RNA
                        organism = synthetic construct
SEQUENCE: 17
ccagacgcat ccctgaggcc                                              20
```

```
SEQ ID NO: 18          moltype = RNA  length = 20
FEATURE                Location/Qualifiers
source                 1..20
                       mol_type = other RNA
                       organism = synthetic construct
SEQUENCE: 18
cgcggtgaca cacaaacatc                                              20

SEQ ID NO: 19          moltype = RNA  length = 19
FEATURE                Location/Qualifiers
source                 1..19
                       mol_type = mRNA
                       organism = Homo sapiens
SEQUENCE: 19
ggctcaagca tggattcta                                               19

SEQ ID NO: 20          moltype = RNA  length = 19
FEATURE                Location/Qualifiers
source                 1..19
                       mol_type = mRNA
                       organism = Homo sapiens
SEQUENCE: 20
gtctcaagtc aaatggatt                                               19

SEQ ID NO: 21          moltype = RNA  length = 19
FEATURE                Location/Qualifiers
source                 1..19
                       mol_type = mRNA
                       organism = Homo sapiens
SEQUENCE: 21
gtgttaagtg aaatgatac                                               19

SEQ ID NO: 22          moltype = DNA  length = 26
FEATURE                Location/Qualifiers
source                 1..26
                       mol_type = other DNA
                       organism = unidentified
SEQUENCE: 22
atcaaggtgc atgtgacact gtgact                                       26

SEQ ID NO: 23          moltype = AA  length = 7
FEATURE                Location/Qualifiers
source                 1..7
                       mol_type = protein
                       organism = unidentified
SEQUENCE: 23
IKVHVTL                                                            7
```

What is claimed is:

1. An antisense oligonucleotide comprising one or more of the sequences selected from:

SEQ ID NO: 15;

SEQ ID NO: 16;

SEQ ID NO: 17; and

SEQ ID NO: 18, wherein each nucleotide comprises a ribose sugar modification, and wherein the antisense oligonucleotide is characterized in that the sequence: (i) specifically binds an ELAV-like RNA-binding protein 3 (ELAVL3) cryptic exon DNA or RNA sequence in a cell when introduced into the cell; and (ii) increases ELAVL3 protein expression in the cell relative to a cell in which the antisense oligonucleotide has not been introduced.

2. The antisense oligonucleotide of claim 1, further characterized in that the sequence increases stathmin-like 2 (STMN2) protein expression in the cell relative to a cell in which the antisense oligonucleotide has not been introduced.

3. The antisense oligonucleotide of claim 1, wherein the ribose sugar modification comprises a 2'-O-methoxyethyl (MOE) modification on each ribose sugar.

4. The antisense oligonucleotide of claim 1, wherein the ribose sugar modification comprises 2'-O-methylribose, 2'-O-methoxyethyl ribose, or 2'fluororibose.

5. The antisense oligonucleotide of claim 1, wherein the sugar modification comprises a locked nucleic acid (LNA) modification.

6. The antisense oligonucleotide of claim 5, wherein the LNA is 1-(hydroxymethyl)-2,5-dioxabicyclo[2.2.1]heptan-7-ol.

7. The antisense oligonucleotide of claim 1, wherein two or more adjacent nucleosides are connected via a modified phosphate linkage.

8. The antisense oligonucleotide of claim 7, wherein the phosphate linkage is a phosphorothioate, methylphosphonate, or phosphorodiamidate linkage.

9. The antisense oligonucleotide of claim 1, wherein two or more adjacent nucleosides are connected by a phosphorothioate linkage, and wherein the ribose sugar modification comprises a 2'-O-methoxyethyl (MOE) modification on each ribose sugar.

10. The antisense oligonucleotide of claim 1, further comprising a nucleobase modification.

11. The antisense oligonucleotide of claim 10, wherein the nucleobase modification comprises a G-clamp nucleotide.

12. The antisense oligonucleotide of claim 11, wherein the G-clamp nucleotide is selected from [9-(2-aminoethoxy)-3H-benzo[b]pyrimido[4,5-e][1,4]oxazin-2(10H)-one]nucleobase, 1-(2-((2-oxo-2,10-dihydro-3H-benzo[b]pyrimido[4,5-e][1,4]oxazin-9-yl)oxy)ethyl)guanidine nucleobase, and 8-(3-aminopropoxy)-3H-benzo [b]pyrimido[4,5-e][1,4]oxazin-2(10H)-one nucleobase, or analogues thereof.

13. A recombinant vector encoding the antisense oligonucleotide of claim 1.

14. A lipid particle comprising the antisense oligonucleotide of claim 1.

15. A pharmaceutical composition comprising the antisense oligonucleotide of claim 1.

16. A method for treating a neurodegenerative disease, the method comprising administering an effective amount of the antisense oligonucleotide of claim 1, a recombinant vector encoding the antisense oligonucleotide of claim 1, or a pharmaceutical composition comprising either or both of the antisense oligonucleotide and the recombinant vector, to a subject in need thereof.

17. An antisense oligonucleotide comprising the RNA sequence SEQ ID NO: 15, wherein two or more adjacent nucleosides of the antisense oligonucleotide are connected via a modified phosphate linkage, and wherein the antisense oligonucleotide comprises an MOE modification.

18. A method for treating a neurodegenerative disease, the method comprising administering an effective amount of the antisense oligonucleotide of claim 17, a recombinant vector encoding the antisense oligonucleotide of claim 17, or a pharmaceutical composition comprising either or both of the antisense oligonucleotide and the recombinant vector, to a subject in need thereof.

19. An antisense oligonucleotide comprising one or more of the DNA sequences selected from:

SEQ ID NO: 6;

SEQ ID NO: 7;

SEQ ID NO: 8; and

SEQ ID NO: 9, wherein each nucleotide comprises a deoxyribose sugar modification, and wherein the antisense oligonucleotide is characterized in that the sequence or segment: (i) specifically binds an ELAV-like RNA-binding protein 3 (ELAVL3) cryptic exon DNA or RNA sequence in a cell when introduced into the cell; and (ii) increases ELAVL3 protein expression in the cell relative to a cell in which the antisense oligonucleotide has not been introduced.

20. A method for treating a neurodegenerative disease, the method comprising administering an effective amount of the antisense oligonucleotide of claim 19, a recombinant vector encoding the antisense oligonucleotide of claim 19, or a pharmaceutical composition comprising either or both of the antisense oligonucleotide and the recombinant vector, to a subject in need thereof.

* * * * *